US009447262B2

(12) United States Patent
York

(10) Patent No.: US 9,447,262 B2
(45) Date of Patent: Sep. 20, 2016

(54) RUBBER COMPOSITION CONTAINING BLOCKED MERCAPTOSILANES AND ARTICLES MADE THEREFROM

(75) Inventor: William M. York, New Fairfield, CT (US)

(73) Assignee: Momentive Performance Materials Inc., Waterford, NY (US)

( * ) Notice: Subject to any disclaimer, the term of this patent is extended or adjusted under 35 U.S.C. 154(b) by 664 days.

(21) Appl. No.: 13/038,507

(22) Filed: Mar. 2, 2011

(65) Prior Publication Data

US 2012/0225231 A1  Sep. 6, 2012

(51) Int. Cl.
| | |
|---|---|
| *B60C 1/00* | (2006.01) |
| *C08L 7/00* | (2006.01) |
| *C08L 9/06* | (2006.01) |
| *C08L 9/00* | (2006.01) |
| *C07F 7/18* | (2006.01) |
| *C08K 5/548* | (2006.01) |

(52) U.S. Cl.
CPC . *C08L 9/06* (2013.01); *B60C 1/00* (2013.01); *C07F 7/1836* (2013.01); *C08K 5/548* (2013.01); *C08L 7/00* (2013.01); *C08L 9/00* (2013.01); *Y10T 428/139* (2015.01)

(58) Field of Classification Search
CPC .............. C08L 7/00; C08L 9/00; C08L 9/06; B60C 1/00; C07K 5/548; C07F 7/0885; C07F 7/1836; C07F 9/4012; Y10T 428/139
USPC ................ 106/481; 428/36.9; 523/150, 351; 524/430, 444, 445, 451, 526, 262
See application file for complete search history.

(56) References Cited

U.S. PATENT DOCUMENTS

| | | | |
|---|---|---|---|
| 3,692,612 A | 9/1972 | Berger | |
| 3,922,436 A | 11/1975 | Bell et al. | |
| 4,709,065 A | 11/1987 | Yoshioka et al. | |
| 5,110,969 A | 5/1992 | Dittrich et al. | |
| 5,116,886 A | 5/1992 | Wolff et al. | |
| 5,663,226 A | 9/1997 | Scholl et al. | |
| 5,780,531 A | 7/1998 | Scholl | |
| 5,827,912 A | 10/1998 | Scholl | |
| 5,977,225 A | 11/1999 | Scholl et al. | |
| 6,020,439 A | 2/2000 | Ko et al. | |
| 6,127,468 A | 10/2000 | Cruse et al. | |
| 6,211,345 B1 | 4/2001 | Weller et al. | |
| 6,268,421 B1 | 7/2001 | Dittrich et al. | |
| 6,350,797 B1 | 2/2002 | Weller | |
| 6,359,046 B1 | 3/2002 | Cruse | |
| 6,414,061 B1 | 7/2002 | Cruse et al. | |
| 6,528,673 B2 | 3/2003 | Cruse et al. | |
| 6,608,125 B2 | 8/2003 | Cruse et al. | |
| 6,649,684 B1 | 11/2003 | Okel | |
| 6,683,135 B2 | 1/2004 | Cruse et al. | |
| 6,759,545 B2 | 7/2004 | Yanagisawa et al. | |
| 6,777,569 B1 | 8/2004 | Westmeyer et al. | |
| 7,074,876 B2 | 7/2006 | Cruse et al. | |
| 7,078,551 B2 | 7/2006 | Cruse et al. | |
| 7,081,500 B2 | 7/2006 | Cruse et al. | |
| 7,122,590 B2 | 10/2006 | Cruse et al. | |
| 7,301,042 B2 | 11/2007 | Cruse | |
| 7,687,558 B2 | 3/2010 | Cruse et al. | |
| 7,696,269 B2 | 4/2010 | Cruse et al. | |
| 7,737,202 B2 | 6/2010 | Cruse et al. | |
| 2003/0130388 A1 | 7/2003 | Luginsland et al. | |
| 2003/0200900 A1 | 10/2003 | Korth et al. | |
| 2004/0220307 A1 | 11/2004 | Wu | |
| 2005/0009955 A1 | 1/2005 | Cohen | |
| 2006/0014870 A1* | 1/2006 | Cruse et al. | 524/262 |
| 2006/0183866 A1 | 8/2006 | Pohl et al. | |
| 2006/0235236 A1 | 10/2006 | Simandan | |
| 2007/0083011 A1 | 4/2007 | Pohl et al. | |
| 2008/0161461 A1 | 7/2008 | Cruse et al. | |
| 2008/0161590 A1* | 7/2008 | Cruse et al. | 556/429 |
| 2010/0174019 A1 | 7/2010 | Cruse et al. | |
| 2010/0179279 A1 | 7/2010 | Cruse et al. | |
| 2010/0256273 A1 | 10/2010 | Cruse et al. | |

FOREIGN PATENT DOCUMENTS

| | | |
|---|---|---|
| AU | 10082/97 A | 7/1997 |
| EP | 9631982 A2 | 1/1995 |
| EP | 1270657 A1 | 1/2003 |
| FR | 2940301 | 6/2010 |
| JP | 63270751 A | 11/1988 |
| JP | 2008-101158 | 5/2008 |
| JP | 2009-167238 | 7/2009 |
| JP | 2010-514764 | 5/2010 |
| JP | 2010-514908 | 5/2010 |
| WO | 2004000930 A1 | 12/2003 |
| WO | 2008/083246 A2 | 7/2008 |
| WO | 2008/085415 A1 | 7/2008 |

OTHER PUBLICATIONS

M.G. Voronkov et al., Zhurnal Obshchei Khimii (1975), 45(6), 1395.
G.A. Gornowicz et al., J. Org. Chem. (1968),33(7),2918-24.

* cited by examiner

*Primary Examiner* — Angela C Scott
(74) *Attorney, Agent, or Firm* — James C. Abruzzo

(57) ABSTRACT

A particulate-filled rubber composition contains at least one silane-reactive particulate filler and a mixture of at least one blocked mercaptosilane coupling agent possessing two thioacyl groups and at least one blocked mercaptosilane possessing a single thioacyl group.

28 Claims, No Drawings

US 9,447,262 B2

RUBBER COMPOSITION CONTAINING BLOCKED MERCAPTOSILANES AND ARTICLES MADE THEREFROM

BACKGROUND OF THE INVENTION

This invention relates to a mineral-filled rubber composition derived in part from sulfur-containing silane coupling agents and articles made from the rubber composition such as tires, tire components, power transmission belts, etc.

Known sulfur-containing silane coupling agents employed in the production of mineral-filled rubbers (elastomers) contain one or more of the following chemical bond types: SH (mercapto), S—S (disulfide or polysulfide), C=S (thiocarbonyl) and C(=O)S (thioester).

Mercaptosilanes exhibit high chemical reactivity for known and conventional organic polymers used in mineral-filled elastomers and therefore effect coupling at substantially reduced loadings. However, the chemical bonds between mercaptosilane coupling agents and organic polymers tend to be weaker than the carbon-carbon bonds of the organic polymers. Under high stress and/or high frequency use conditions, these chemical bonds are susceptible to breakage and, therefore, loss or reduction of coupling between the organic polymer and the coupling agent. This loss or reduction of coupling may contribute to the wear and/or degradation of other important physical properties of rubber compositions formulated with mercaptosilane coupling agents. The high chemical reactivity of mercaptosilane coupling agents with organic polymers also leads to unacceptably high viscosities'during processing and/or premature curing (scorch). Their undesirability is further aggravated by their highly disagreeable odor. As a result, other less reactive coupling agents such as those containing the S—S (disulfide or polysulfide) linkage and C=S (thiocarbonyl) or C(=O)S (thioester) functional groups are used alone or in admixture with mercaptosilane coupling agents in order to reduce the high chemical reactivity of the latter. Because these less reactive silane coupling agents generally contain a single sulfur functional group capable of reacting with the organic polymers, the relatively weak C—S bond may break when the rubber is subjected to high stress use conditions leading to decoupling of the rubber from the mineral filler, formation of voids and/or tearing of the filled rubber which manifests itself most commonly as wear.

M. G. Voronkov et al., Zhumal Obshchei Khimii (1975), 45(6), 1395, discloses acylthioalkyl silanes such as $CH_3C(=O)S(CH_2)_{1-3}Si(OR)_3$. U.S. Pat. No. 3,922,436 discloses the sulfur silane $HOC(=O)CH_2CH_2C(=O)S(CH_2)_3Si(OC_2H_5)_3$ and its use as a coupling agent. This silane contains only a single blocked mercapto group.

JP 63270751 discloses the use of compounds represented by the general formula $CH_2=C(CH_3)C(=O)S(CH_2)_{1-6}Si(OCH_3)_3$ in tire tread compositions. These compounds contain only a single blocked mercapto group and are generally undesirable due to the potential of the unsaturation α,β to the carbonyl group of the thioester to undergo polymerization during the compounding process or during storage.

Australian Patent AU-A-10082/97 discloses the use in rubber of silanes of the structure $R^1{}_nX_{3-n}Si$-$(Alk)_m(Ar)_p$—$S(C=O)$—$R$ where $R^1$ is phenyl or alkyl; X is halogen, alkoxy, cycloalkoxy, acyloxy or OH; Alk is alkyl; Ar is aryl; R is alkyl, alkenyl or aryl; n is 0 to 2; and, m and p are each 0 or 1 but both cannot be zero. However, it is stipulated that compositions containing these silanes must be used in conjunction with functionalized siloxanes.

U.S. Pat. Nos. 6,608,125; 6,683,135; 6,204,39; 6,127,468; 6,777,569; 6,528,673; and, 6,649,684, U.S. published patent application Nos. 2005/0009955, 2004/0220307, 2003/020900 and 2003/0130388, pending U.S. patent application Ser. Nos. 11/105,916 and 10/128,804 and EP 1 270 657 disclose the use of blocked mercaptosilanes of the structure $[[(ROC(=O))_p\text{-}(G)_j]_k\text{—}Y\text{—}S]_r\text{-}G\text{-}(SiX_3)_s$ where Y is a polyvalent blocking group, r is an integer of from 1 to 3 and s is preferably from 1 to 3, in rubber master batches and as a surface treatment for mineral fillers. Although these patents and patent applications disclose coupling agents, that possess more than one blocked mercapto group, i.e., compounds in which r=2 or 3, they do not describe the specific stereochemical configurations of the polyvalent G structure between the silicon atom and the organofunctional group necessary to achieve efficient multiple bonding with the organic polymer component(s) of the rubber formulations.

U.S. Pat. Nos. 6,359,046; 5,663,226; 5,780,531; 5,827,912; 5,977,225; 4,709,065 and 6,759,545 and WO 2004000930 disclose a class of polysulfide silane coupling agents that on average contain more than one S—S (disulfide or polysulfide) linkage per molecule. However, the multiple S—S linkages are achieved by separating individual linkages with an organic hydrocarbon radical. In use, these S—S groups decompose to form sulfur radicals that couple to the polymer but generate species that contain only one sulfur reactive group per silicon atom. The polysulfide silane coupling agents disclosed in U.S. Pat. Nos. 5,110,969, 6,268,421, 6,211,345 and 6,350,797 overcome this drawback by containing more than one sulfur functional group directly bonded to a silicon atom through a cyclic hydrocarbon radical. The multiple S—S groups are bonded to adjacent carbon atoms and the silicon atoms are directly bonded to the ring structures through hydrosilation of the alkoxysilane with vinyl-containing cyclic hydrocarbons. However, these compounds contain rings of S—S and carbon atoms or are polymeric materials wherein the silyl-containing hydrocarbon radicals are bonded through S—S groups. These cyclic or polymeric coupling agents are less reactive for organic polymers because they contain S—S groups bonded directly to secondary carbon atoms. The bonding of the S—S-containing group to secondary carbon atoms sterically hinders the reaction of the S—S groups and inhibits their reaction with the organic polymers.

U.S. published patent application No. 2008/0161590 discloses sulfur silanes containing multiple blocked mercapto groups and the use of the silanes in rubber. These sulfur silanes form multiple attachments to the rubber and effectively couple the rubber to the mineral filler. However, due to the relatively large bulky cyclo group, the filler can possess regions that do not contain silane coupling agent.

Therefore, a need exists for sulfur-containing silane coupling agents that have low reactivity to provide processing of the mineral-filled elastomers or rubbers but without scorch, that aid in the effective dispersion of the mineral filler within the rubber matrix and that can be activated at the desired time to form multiple linkages with the organic polymer component(s). These multiple linkages provide sufficient bonding so that the loss of coupling between the rubber and coupling agent is minimized during high stress use conditions, such as those experienced by tires, without exhibiting the disadvantages described above.

BRIEF DESCRIPTION OF THE INVENTION

The present invention is directed to a particulate-filled rubber composition containing a mixture of at least one blocked mercaptosilane containing a single blocked mercapto group and at least one blocked mercaptosilane containing two blocked mercapto groups bonded to a cyclic hydrocarbon through straight chain alkylene groups.

Blocked mercaptosilanes are compounds in which the mercapto hydrogen atom is replaced with another group (hereafter referred to as "blocking group") and possess an alkoxysilyl group. Specifically, the silanes of the present invention are blocked mercaptosilanes in which the blocking group contains an acyl group bonded directly to sulfur via a single bond.

More particularly, the present invention is directed to a particulate-filled rubber composition comprising:
(i) at least one vulcanizable rubber;
(ii) at least one silane-reactive particulate filler;
(iii) at least one blocked mercaptosilane possessing two thioacyl groups, the blocked mercaptosilane having the formula:

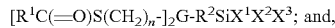
$[R^1C(=O)S(CH_2)_n-]_2G-R^2SiX^1X^2X^3$; and, (iv) at least one blocked mercaptosilane possessing a single thioacyl group, the blocked mercaptosilane having the formula:

$R^3C(=O)SR^4SiX^1X^2X^3$, wherein
$R^1$, each occurrence, is independently hydrogen or a monovalent hydrocarbon group containing up to 12 carbon atoms;
$R^2$ is a divalent hydrocarbon group containing up to 10 carbon atoms and, optionally, an oxygen atom or sulfur atom;
$R^3$ is hydrogen or a monovalent hydrocarbon group containing up to 18 carbon atoms;
$R^4$ is a divalent hydrocarbon group containing up to 12 carbon atoms;
G is a trivalent cyclic hydrocarbon group containing up to 10 carbon atoms;
$X^1$, each occurrence, is independently selected from the group consisting of $R^5O-$ and $R^5C(=O)O-$, wherein $R^5$ is hydrogen or a monovalent hydrocarbon group containing up to 18 carbon atoms and, optionally, at least one oxygen atom;
$X^2$ and $X^3$, each occurrence, is independently chosen from the group consisting of the members listed for $R^6$ and $X^1$, wherein $R^6$ is a monovalent hydrocarbon group of up to 6 carbon atoms; and,
n is an integer from 1 to 5.

The present invention also includes a process for making the foregoing particulate-filled rubber composition, a free-flowing filler composition prepared from silane-reactive particulate filler (ii) and mixture of blocked mercaptosilanes (iii) and (iv) and a rubber composition containing the free-flowing filler composition.

In still other embodiments, the present invention provides a cured rubber and articles made therefrom.

The entire contents of all prior patent and non-patent publications cited herein are incorporated by reference herein.

The term "elastomer" is synonymous, and therefore interchangeable, with "rubber".

The term "vulcanized" is synonymous, and therefore interchangeable, with "cured".

The expression "inert particulate filler" shall be understood to apply to particulate filler materials that are essentially nonreactive with silanes.

The expression "blocked mercaptosilane(s)" shall be understood to include partial hydrolyzates. Partial hydrolyzates of blocked mercaptosilanes (iii) and (iv) result from most methods for their manufacture and/or can occur upon their storage, especially under humid conditions.

The expression "coupling agent" means an agent capable of establishing an effective chemical and/or physical bond between a vulcanizable elastomer and its filler. Effective coupling agents have functional groups capable of bonding physically and/or chemically with filler, for example, between a silicon atom of the coupling agent and the hydroxyl (OH) surface groups of the filler (e.g., surface silanols in the case of silica), and, for example, sulfur atoms which are capable of bonding physically and/or chemically with the elastomer as a result of vulcanization (curing).

The term "filler" means a substance that is added to the elastomer to either extend the elastomer or to reinforce the elastomeric network. Reinforcing fillers are materials whose moduli are higher than the organic polymer of the elastomeric composition and are capable of absorbing stress from the organic polymer when the elastomer is strained. Fillers include fibers, particulates, and sheet-like structures and can be composed of inorganic minerals, silicates, silica, clay, ceramics, carbon, organic polymer and diatomaceous earth. The rubber composition herein must contain at least one silane-reactive particulate filler and may optionally contain one or more particulate fillers that are essentially inert to silane.

The term "carrier" means a porous or high surface area filler that has a high adsorption or absorption capability and is capable of carrying up to 75 percent liquid silane while maintaining its free-flowing and dry properties. Useful filler/carriers herein are essentially inert to silane coupling agents and are capable of releasing or deabsorbing liquid silanes when added to the vulcanizable rubber composition.

The term, "hydrocarbon" as used herein refers to any chemical structure containing hydrogen atoms and carbon atoms and, optionally, structures in which the carbon-carbon bonding in the backbone is interrupted by bonding to atoms of oxygen and/or sulfur and/or strictures in which a hydrogen or two hydrogens bonded to carbon are replaced with an oxygen or sulfur atom such as a primary alcohol (—OH), or an oxo (=O).

As used herein, "alkyl" includes straight, branched and cyclic alkyl groups; "alkenyl" includes any straight, branched or cyclic alkenyl group containing one or more carbon-carbon double bonds where the point of substitution can be either at a carbon-carbon double bond or elsewhere in the group; and, "alkynyl" includes any straight, branched or cyclic alkynyl group containing one or more carbon-carbon triple bonds and, optionally, one or more carbon-carbon double bonds where the point of substitution can be either at a carbon-carbon triple bond, a carbon-carbon double bond or elsewhere in the group.

Specific, non-limiting examples of alkyl groups include methyl, ethyl, propyl and isobutyl. Specific, non-limiting examples of alkenyls include vinyl, propenyl, allyl and methallyl. Specific, non-limiting examples of alkynyls include acetylenyl, propargyl and methylacetylenyl.

As used herein, "aryl" includes any aromatic hydrocarbon from which one hydrogen atom has been removed; "aralkyl" includes any of the aforementioned alkyl groups in which one or more hydrogen atoms have been substituted by the same number of like and/or different aryl (as defined herein) substituents; and "arenyl" includes any of the aforementioned aryl groups in which one or more hydrogen atoms have been substituted by the same number of like and/or different alkyl (as defined herein) substituents. Specific, non-limiting examples of aryl groups include phenyl and naphthalenyl. Specific, non-limiting examples of aralkyl groups include benzyl and phenethyl. Specific, non-limiting examples of arenyl groups include tolyl and xylyl.

Other than in the working examples or where otherwise indicated, all numbers expressing amounts of materials, reaction conditions, time durations, quantified properties of materials, and so forth, stated in the specification and claims are to be understood as being modified in all instances by the term "about".

It will be understood that any numerical range recited herein includes all sub-ranges with that range and any combination of the various endpoints of such ranges or sub-ranges.

It will be further understood that any compound, material or substance which is expressly or implicitly disclosed in the specification and/or recited in a claim as belonging to a group of structurally, compositionally and/or functionally related compounds, materials or substances includes individual representatives of the group and all combination thereof.

DETAILED DESCRIPTION OF THE INVENTION

Vulcanizable Rubber (i)

Suitable vulcanizable, i.e., curable, rubbers (organic polymers) are well known in the art and are described in numerous texts of which two examples are *The Vanderbilt Rubber Handbook*, R. F. Ohm, ed. (R.T. Vanderbilt Company, Inc., Norwalk, Conn., 1990), and *Manual for the Rubber Industry*, T. Kempermann, S. Koch, and J. Sumner, eds. (Bayer A G, Leverkusen, Germany, 1993).

Representative examples of suitable vulcanizable polymers include solution polymerization-prepared styrene-butadiene rubber (sSBR), styrene-butadiene rubber (SBR), natural rubber (NR), polybutadiene (BR), ethylene-propylene co- and ter-polymers (EP, EPDM) and acrylonitrile-butadiene rubber (NBR). The rubber composition herein is comprised of at least one diene-based elastomer, or rubber. Suitable conjugated dienes are isoprene and 1,3-butadiene and suitable vinyl aromatic compounds are styrene and alpha methyl styrene.

The diene-based elastomer, or rubber, may be selected, for example, from at least one of cis-1,4-polyisoprene rubber (natural and/or synthetic, and preferably natural, rubber), emulsion polymerization-prepared styrene/butadiene copolymer rubber, organic solution polymerization-prepared styrene/butadiene rubber, 3,4-polyisoprene rubber, isoprene/butadiene rubber, styrene/isoprene/butadiene terpolymer rubber, cis-1,4-polybutadiene, medium vinyl polybutadiene rubber (35 percent to 50 percent vinyl), high vinyl polybutadiene rubber (50 percent to 75 percent vinyl), styrene/isoprene copolymers, emulsion polymerization-prepared styrene/butadiene/acrylonitrile terpolymer rubber and butadiene/acrylonitrile copolymer rubber. Also useful are an emulsion polymerization-derived styrene/butadiene (eSBR) having a relatively conventional styrene content of 20 percent to 28 percent bound styrene or, for some applications, an eSBR having a medium to relatively high bound styrene content, namely, a bound styrene content of 30 percent to 45 percent. Emulsion polymerization-prepared styrene/butadiene/acrylonitrile terpolymer rubbers containing 2 to 40 weight percent bound acrylonitrile in the terpolymer are also contemplated as diene-based rubbers for use in this invention.

The solution polymerization-prepared SBR typically has a bound styrene content in a range of 5 to 50 percent, preferably 9 to 36 percent. Polybutadiene elastomer may be conveniently characterized, for example, by having at least a 90 weight percent cis-1,4-content.

The amount of each the rubber components in the formulation is added together and the sum is normalized to a value of 100 parts per hundred parts rubber.

Silane-Reactive Particulate Filler (ii)

Suitable silane-reactive particulate fillers include metal oxides such as silica (pyrogenic and precipitated), titanium dioxide, alumina and aluminosilicates, siliceous materials such as clays and talc, and their mixtures. Optionally, inert, i.e., silane-nonreactive, filler(s) such as carbon black, acetylene black, calcium carbonate, and barium sulfate may be employed along with silane-reactive particulate filler(s) (ii). A combination of silica and carbon black is particularly advantageous for use in rubber products such as tire tread. Alumina can be used either alone or in combination with silica. The term "alumina" herein refers to aluminum oxide, or $Al_2O_3$. The fillers may be in hydrated or anhydrous form. Use of alumina in rubber compositions is described, for example, in U.S. Pat. No. 5,116,886 and in EPO 0 631,982.

In some embodiments, and as more fully described herein, at least part of silane-reactive particulate filler (ii) is reacted with a mixture of at least part of blocked mercaptosilane (iii) and at least part of blocked mercaptosilane. In other embodiments, the full amounts of blocked mercaptosilanes (iii) and (iv) can be added to the rubber mix during the rubber and filler mixing, or processing, stage. Where blocked mercaptosilanes (iii) and (iv) and filler are added separately to the rubber mix during the rubber and filler mixing, or processing, stage, they can be regarded as being mixed in situ with the filler.

The vulcanized rubber composition will ordinarily contain a sufficient amount of silane-reactive particulate filler(s) to contribute a reasonably high modulus and high resistance to tear. The weight of the silane-reactive particulate filler(s) may be as low as 5 phr and as high as 140 phr, and is preferably from 25 phr to 110 phr.

In one embodiment of the present invention, precipitated silica is used as the silane-reactive filler. The preferred silicas may be characterized by having a BET surface area, as measured using nitrogen gas, preferably in the range of from 40 to 600 m²/g and more usually in a range of from 50 to 300 m²/g. The preferred silicas may also be characterized by having a dibutylphthalate (DBP) absorption value in a range of from 100 to 350 and more usually from 150 to 300. Furthermore, silica filler, as well as the aforesaid alumina and aluminosilicate fillers, may be characterized by having a CTAB surface area in a range of 100 to 240. The CTAB surface area is the external surface area as measured with cetyl trimethylammonium bromide at a pH of 9 employing the method of ASTM D 3849.

Mercury porosity surface area is the specific surface area as determined by the mercury porosimetry method. According to this method, mercury is allowed to penetrate into the pores of a measured sample of particulate filler after a thermal treatment to remove volatiles therefrom. Typical set-up conditions include a 100 mg sample, removing volatiles over a two hour period at 105° C. and ambient atmospheric pressure and a pressure ranging from ambient to 2000 bars. The mercury porosimetry method may be performed in accordance with that described in Winslow, Shapiro in ASTM bulletin, page 39 (1959) or according to DIN 66133. For such a method, a CARLO-ERBA Porosimeter 2000 may be used. The average mercury porosity specific surface area for a typical silica filler can range from 100 to 300 m$^2$/g.

A suitable pore size distribution for the silica, alumina and aluminosilicate fillers according to the foregoing mercury porosity determination method can be: 5 percent or less of its pores have a diameter of less than about 10 nm; from 60 percent to 90 percent of its pores have a diameter of 10 to 100 nm; from 10 percent to 30 percent of its pores have a diameter of from 100 to 1,000 nm; and from 5 percent to 20 percent of its pores have a diameter of greater than about 1,000 nm.

The silica might be expected to have an average ultimate particle size, for example, in the range of from 0.01 to 0.05 μm as determined by electron microscopy although the silica particles may be even smaller, and even larger, in size. Various commercially available silicas are useful in this invention such as those from PPG Industries under the HI-SIL trademark with designations HI-SIL 210, 243, etc.; silicas available from Rhodia, with, for example, the designation ZEOSIL 1165 MP, Zeosil 195HR, and Zeosil Premium 200MP; silicas available from Evonik Industries with, for example, designations VN2 and VN3, and Ultrasil 7000GR, etc.; and, silicas commercially available from Huber having, for example, the designation HUBERSIL 8745.

In one embodiment of the present invention, where it is desired for the rubber composition to contain both a siliceous filler such as silica, alumina and/or an aluminosilicate and carbon black as a filler/reinforcing pigment, it is often preferable that the weight ratio of the siliceous filler(s) to carbon black be at least 3/1, preferably at least 10/1 and up to 30/1. The filler can be comprised of from 15 to 95 weight percent precipitated silica, alumina and/or aluminosilicate and, correspondingly from 5 to 85 weight percent carbon black wherein the carbon black has a CTAB value in a range of from 80 to 150. Alternatively, the filler can be comprised of from 60 to 95 weight percent of said silica, alumina and/or aluminosilicate and, correspondingly, from 40 to 5 weight percent carbon black. The siliceous filler(s) and carbon black filler can be preblended or blended together in the manufacture of the vulcanized rubber.

Blocked Mercaptosilanes (iii) and (iv)

Blocked mercaptosilanes (iii) and (iv), supra, are useful in admixture as coupling agents for vulcanizable organic polymer(s) (i.e., rubber(s)) (i) and silane-reactive particulate filler(s) (ii). The mixture of blocked mercaptosilanes (iii) and (iv) are unique in that the high efficiency of the mercapto group can be exploited unaccompanied by the detrimental side effects typically associated with the use of mercaptosilanes such as high processing viscosity, less than desirable filler dispersion, premature curing (scorch) and odor. These benefits are realized due to the mercaptan group being initially unavailable for reaction with the rubber component(s) (i) as a resulting of its blocking group. Generally, only the reaction of the silane —SiX$^1$X$^2$X$^3$ group with the silane-reactive filler can occur during the initial stage of the compounding process. Thus, substantial coupling of the filler to the polymer is precluded during mixing thereby minimizing undesirable premature curing (scorch) and the associated undesirable increase in viscosity. One can achieve better cured filled rubber properties, such as a balance of high modulus and abrasion resistance, as a consequence of preventing, inhibiting or minimizing premature curing.

The number of carbon atoms in the R$^2$ group which bonds the silicon atom to the G group, and the number of methylene units between the blocked mercaptan and the G group, denoted by n, improves coupling clue to the R$^2$ group and methylene groups ability to mitigate excessive steric interactions between mercaptosilane (iii) and the filler and polymer. Two or more successive methylene groups mitigate steric interactions and add flexibility to the chemical structure of mercaptosilane (iii) thereby enhancing its ability to accommodate the positional and orientational constraints imposed by the morphologies of the surfaces of both the rubber and filler at the interphase, i.e., at the molecular level. Tighter structures containing secondary, and especially tertiary, carbon atoms rather than the linear straight chain alkylene group that bonds the thioacyl group to the ring structure, especially, aromatic structures, are more rigid and cannot readily orient to meet available binding sites on the silica and polymer components. This sterically crowded structure resulting from secondary and tertiary carbon atoms would tend to leave sulfur groups unbound to polymer thereby reducing the efficiency by which the multiple bonding of silane to polymer through two unblocked mercapto groups (free mercaptans) on silane, is realized.

The G group is a cyclic structure which is connected to the silyl and blocked mercapto groups through hydrocarbylene linking groups. This structural feature also improves coupling because the geometry of the cyclic structure naturally directs the emanating groups away from each other. The G group keeps these silyl and blocked mercapto groups from getting in each other's way and also forces them to orient in divergent directions so that the silyl group can bond to the filler while, after deblocking, the mercapto group bonds to the polymer phase. Aromatic cyclic structures for G are very rigid and direct silyl and blocked mercapto groups in diverging directions. Their rigidity limits freedom of orientation of the blocked mercapto group, and therefore the number of methylene units, denoted by the integer n, and may need to be larger. The aliphatic cyclic G structures, because they do not contain the conjugated double bonds, are more flexible. They combine the advantages of divergent silyl groups and blocked mercapto groups orientations from a cyclic structure and flexibility of the aliphatic cyclic structure.

Blocked mercaptosilane (iv), which contains a single thioacyl group, is believed to increase the amount of silyl groups bonded to the inorganic filler surface because they tend to be less bulky and can insert themselves between bound blocked mercaptosilanes (iii) which contain two thioacyl groups. The linear long chain geometry of mercaptosilanes (iv) also assist in the dispersion of the inorganic filler by minimizing the amount of surface on the filler that does not contain a silyl group thereby minimizing or eliminating the number of surface hydroxyl groups capable of hydrogen bonding with hydroxyl groups on other filler particles. Hydrogen bonding between filler particles may result in agglomeration and formation of aggregates and/or agglomerates.

Representative non-limiting examples of G include any of the structures derivable from cyclopentane, cyclohexane, cycloheptane, cyclooctane, cyclodecane, cyclododecane, cyclohexene, cyclohexadiene, benzene, toluene, xylene and naphthalene.

Representative, non-limiting examples of R$^1$ include hydrogen, methyl, ethyl, propyl, isopropyl, butyl, hexyl, 2-ethylhexyl, octyl, decyl, cyclohexyl, phenyl, benzyl and phenethyl.

Representative, non-limiting examples of R$^2$ include methylene, ethylene, propylene, isopropylene, butylene, hexylene, octylene, decylene, cyclohexylene and phenylene.

Representative, non-limiting examples of $R^3$ include hydrogen, methyl, ethyl, propyl, isopropyl, butyl, hexyl, 2-ethylhexyl, octyl, decyl, octadecyl, cyclohexyl, phenyl, benzyl and phenethyl.

Representative, non-liming examples of $R^4$ include methylene, ethylene, propylene, isopropylene, butylene, hexylene, octylene, decylene, cyclohexylene and phenylene.

Representative, non-limiting examples of $R^5$ include hydrogen, methyl, ethyl, propyl, isopropyl, butyl, hexyl, 2-ethylhexyl, octyl, decyl, octadecyl, cyclohexyl, phenyl, benzyl, phenethyl, 3-oxabutyl and 4,7-dioxaoctyl.

Representative, non-limiting examples of $R^6$ include methyl, ethyl, propyl, isopropyl, butyl and phenyl.

Representative non-limiting examples of $X^1$ include methoxy, ethoxy, propoxy, isopropoxy, butoxy, phenoxy, benzyloxy, hydroxy and acetoxy. Representative examples of $X^2$ and $X^3$ include the representative examples listed above for $X^1$ as well as methyl, ethyl, propyl, isopropyl, sec-butyl, phenyl, vinyl and cyclohexyl.

In another embodiment of the present invention, $R^1$ is methyl, ethyl or pentyl, G is derived from cyclohexane or benzene, $R^2$ is ethylene, propylene or butylene, $X^1$ is methoxy, ethoxy or propoxy and n is 2 to 4.

In still another embodiment of the present invention, $R^3$ is an alkyl group containing from 5 to 9 carbon atoms and bonded to the carbonyl group through a primary carbon atom, $R^4$ is methylene, ethylene or propylene, $X^1$ is methoxy, ethoxy or propoxy and $X^2$ and $X^3$ individually include the representative examples for $X^1$ and methyl.

In yet another embodiment of the present invention, the amount of blocked mercaptosilane containing two thioacyl groups (iii) in the mixture of the blocked mercaptosilane containing two thioacyl groups (iii) and blocked mercaptosilane containing a single thioacyl groups (iv) is from 10 to 30 weight percent based upon the total weight of the mixture of components (iii) and (iv).

In a further embodiment of the present invention, the sum of the carbon atoms of the $R^3$ and $R^4$ groups within blocked mercaptosilane (iii) can range from 2 to 16, more particularly 6 to 14. This amount of carbon in the $R^3$ and $R^4$ groups facilitates the dispersion of the filler into the organic polymers and can affect the rate of cure thereby improving the balance of properties in the cured filled rubber.

In another embodiment of the present invention, G is derived from cyclohexane, $R^1$ is methyl or ethyl, $R^2$ is ethylene or 3-thia-hexylene, $X^1$ is ethoxy and n=2.

In yet another embodiment, when G is derived from cyclohexane or benzene, the two thioacyl alkylene groups are in the 3,4 positions or the 3,5 positions on the ring. These positions allow for the thioacyl groups, once deblocked, to form free mercapto groups and to form chemical bonds with the rubber to a greater extent than when these groups are substituted in the 2-position. The thioacylalkylene group in the 2 position is directed towards the filler surface where steric hindrance make it more difficult, once deblocked, to form chemical bonds with the rubber.

Blocked mercaptosilanes (iii) and (iv) are generally prepared separately and then mixed together in the desired weight amounts such as those indicated above.

Methods for preparing blocked mercaptosilanes (iii) and (iv) can involve direct incorporation of the thioester group into an alkene-functional silane by free radical addition of a thioacid across the carbon-carbon double bond. This reaction can be catalyzed by UV light, heat or appropriate free radical initiator. The reaction can be carried out at elevated temperatures or by refluxing a mixture of the alkene-functional silane and thioacid. Various aspects of the reaction are described in U.S. Pat. No. 3,692,812 and in G. A. Gornowicz et al., *J. Org. Chem.* (1968), 33(7), 2918-24. The uncatalyzed reaction can occur at temperatures as low as 105° C., but often fails. The probability of success increases with temperature and becomes high when the temperature is 160° C. or greater. The reaction may be made more reliable and brought largely to completion by using UV radiation or a catalyst. With a catalyst, the reaction can be made to occur at temperatures at or below 90° C. Appropriate catalysts include free radical initiators, e.g., air, peroxides, particularly organic peroxides, and azo compounds. Examples of peroxide initiators include peracids such as perbenzoic and peracetic acids; esters of peracids; hydroperoxides such as t-butyl hydroperoxide; peroxides such as di-t-butyl peroxide; and, peroxy-acetals and ketals such as 1,1-bis(t-butylperoxy)cyclohexane. Examples of azo initiators include azobisisobutyronitrile (AIBN), 1,1-azobis(cyclohexanecarbonitrile) (VAZO, DuPont product) and azo-tert-butane.

The reaction can be carried out by heating a mixture of the alkene-functional silane and thioacid reactants with the catalyst of choice. It is preferable for the overall reaction to be run on an equimolar or near equimolar basis in order to obtain optimum conversions. The reaction is sufficiently exothermic that it tends to lead to a rapid temperature increase to reflux followed by vigorous reflux as the reaction continues. This vigorous reaction can lead to hazardous boil-overs in the case of relatively large quantities of reactants. Side reactions, contamination and loss in yield can also result from uncontrolled reactions. In general, the reaction can be effectively controlled by adding partial quantities of one reactant to the other, initiating the reaction with the catalyst, allowing the reaction to run its course largely to completion, and then adding the remaining reactant, either all at once or in increments. The initial concentrations and rate of addition and number of subsequent additions of the deficient reactant will depend on the type and amount of catalyst used, the scale of the reaction, the nature of the starting materials and the ability of the reactor equipment to absorb and dissipate heat. A second way of controlling the reaction would involve the continuous addition of one reactant to the other with concomitant continuous addition of catalyst. Whether continuous or sequential addition is used, the catalyst can be added alone and/or pre-blended with one or both reactants or a combination of these expedients can be employed.

The reflux method of preparation involves initially bringing the alkene-functional silane to a temperature of 160° to 180° C. or to reflux, whichever temperature is lower. The first portion of thioacid is then added at a rate such as to maintain a vigorous, but controlled, reflux. For alkene-functional silanes with boiling points above 100° to 120° C., this reflux results largely from the relatively low boiling point of thioacid (88° to 92° C., depending on purity) relative to the temperature of the alkene-functional silane. At the completion of the addition, the reflux rate rapidly subsides. It often accelerates again within several minutes, especially if an alkene-functional silane with a boiling point above 120° C. is used, as the reaction initiates. If the reaction does not initiate within 10 to 15 minutes, initiation can be brought about by addition of catalyst. A preferred catalyst is di-t-butyl peroxide. An appropriate quantity of catalyst is from 0.2 to 2 percent, more particularly from 0.5 to 1 percent, of the total weight of reaction mixture to which the catalyst is added. The reaction typically initiates within a few minutes as evidenced by an increase in reflux rate. The reflux temperature gradually increases as the reaction proceeds. The next portion of thioacid is then added and the aforementioned sequence of steps is repeated. The preferred number of thioacid additions for total reaction quantities of about one to about four kilograms is two with about one-third of the total thioacid used in the first addition and the remainder in the second. For total quantities in the range of about four to ten kilograms, a total of three thioacid additions is preferred, the distribution being approximately 20 percent of the total used in the first addition, approximately 30 percent in the second addition and the remainder in the third addition. For larger scales involving thioacid and alkene-functional silanes, it is preferably to use more than a total of three thioacid additions and, more preferably, to add the reagents in the reverse order. Initially, the total quantity of thioacid is brought to reflux followed by continuous addition of the alkene-functional silane to the thioacid at such a rate as to bring about a smooth but vigorous reaction rate. The catalyst, e.g., di-t-butylperoxide, can be added in small portions during the course of the reaction or as a continuous flow. It is best to accelerate the rate of catalyst addition as the reaction proceeds to completion in order to obtain the highest yields of product for the lowest amount of catalyst required. The total quantity of catalyst used should be 0.5 to 2 percent of the total weight of reactants. Whichever method is used, the reaction is followed up by a vacuum stripping process to remove volatiles and unreacted thioacid and silane. The product may then be purified by distillation.

In yet another method of preparation, an alkali metal salt of a thioacid is reacted with a haloalkylsilane. The first step involves preparation of a salt of the thioacid. Alkali metal derivatives are preferred with the sodium derivative being more preferred. These salts can be prepared as solutions in solvents in which the salt is appreciably soluble. Suspensions of the salts as solids in solvents in which the salts are only slightly soluble are also useful. Alcohols such as propanol, isopropanol, butanol, isobutanol, and t-butanol, and preferably methanol and ethanol, are especially useful due to the alkali metal salts being only slightly soluble therein. In cases where the desired product is an alkoxysilane, it is preferable to use an alcohol corresponding to the silane alkoxy group so as to prevent transesterification at the silicon ester. Alternatively, nonprotic solvents can be used. Examples of suitable solvents are ethers or polyethers such as glyme, diglyme and dioxanes; N,N-dimethylformamide; N,N-dimethylacetamide; dimethylsulfoxide; N-methylpyrrolidinone; and, hexamethylphosphoramide.

Once a solution, suspension, or combination thereof of the salt of the thioacid has been prepared, the salt is reacted with the selected haloalkylsilane. This may be accomplished by stirring a mixture of the haloalkylsilane with the solution, suspension or combination thereof of the salt of the thioacid at temperatures corresponding to the liquid range of the solvent for a period of time sufficient to substantially complete the reaction. Suitable reaction temperatures are those at which the salt is appreciably soluble in the solvent and at which the reaction proceeds at an acceptable rate without excessive side reactions. With reactions starting from chloroalkylsilanes in which the chlorine atom is not allylic or benzylic, preferable temperatures are in the range of 60° to 160° C. Reaction times can range from one or several hours to several days. For alcohol solvents where the alcohol contains four carbon atoms or fewer, the preferred temperature is at or near reflux. When diglyme is used as a solvent, the preferred temperature is in the range of 70° to 120° C. depending on the thioacid salt used. If the haloalkylsilane is a bromoalkylsilane or a chloroalkylsilane in which the chlorine atom is allylic or benzylic, reductions of 30° to 60° C. in reaction temperature are appropriate due to the greater reactivity of the bromo group. For reactions between straight chain chloroalkylethoxysilanes and sodium thiocarboxylates to form thiocarboxylate ester ethoxysilanes, it is preferable to use ethanol at reflux for 10 to 20 hours provided the presence of from 5 to 20 weight percent mercaptosilane is acceptable in the reaction product. Otherwise, it may be preferred to employ diglyme as the solvent in which case the reaction can be carried out within the range of 80° to 120° C. for from one to three hours. Upon completion of the reaction, the salts and solvent will ordinarily be removed followed by distillation of the reaction product to provide higher purity.

If the salt of the thioacid is not commercially available, its preparation may be accomplished by one of two methods described below as Method A and Method B. Method A involves adding the alkali metal or a base derived from the alkali metal to the thioacid. The reaction occurs at ambient temperature. Appropriate bases include alkali metal alkoxides, hydrides, carbonates and bicarbonates. Solvents such as toluene, xylene, benzene, aliphatic hydrocarbons, ethers and alcohols may be used to prepare the alkali metal derivatives. In Method B, acid chlorides or acid anhydrides are converted directly to the salt of the thioacid by reaction with alkali metal sulfide or hydrosulfide. Hydrated or partially hydrous alkali metal sulfides or hydrosulfides are commercially available; however, anhydrous or nearly anhydrous alkali metal sulfides or hydrosulfides are preferred. Hydrous materials can be used, however, but with loss in yield and hydrogen sulfide formation as a co-product. The reaction involves addition of the acid chloride or acid anhydride to the solution or suspension of the alkali metal sulfide and/or hydrosulfide and heating at temperatures ranging from ambient to the reflux temperature of the solvent for a period of time sufficient substantially to complete the reaction as indicated by the formation of co-product salts.

If the alkali metal salt of the thioacid is prepared in such a way that an alcohol is present, either for having been used as solvent or having been formed, for example by the reaction of thioacid with alkali metal oxide removal of the alcohol may be desired if a product low in mercaptosilane is to be obtained. In such a case, it is necessary to remove the alcohol prior to reaction of the salt of the thioacid with the haloalkylsilane. This can be achieved by distillation or evaporation. Alcohols such as methanol, ethanol, propanol, isopropanol, butanol, isobutanol and t-butanol are preferably removed by azeotropic distillation with benzene, toluene, xylene or aliphatic hydrocarbons. Toluene and xylene are preferred for this purpose.

In still another method of preparation, mercaptosilanes (iii) and (iv) can be obtained by a two-phase reaction between alkali metal salt of a thioacid and a haloalkylsilane. The alkali metal salt is soluble in the aqueous phase while the haloalkylsilane has only limited solubility therein, thereby forming an organic phase. The reactions can be run at temperatures ranging from 15° to 95° C. under atmospheric pressures or at higher temperatures if the pressure is increased to prevent boiling of the water phase. Phase transfer catalysts such as n-butylammonium bromide or hexaethyl guanidine can be used to increase the solubility of the alkali metal thioacid salt in the organic phase which will increase the reaction rate, shorten the reaction times and minimize the hydrolysis of the alkoxysilyl groups.

Representative examples of blocked mercaptosilane (iii) of the present invention include, but are not limited to, 1-(2-triethoxysilylethyl)-3,5-bis-(3-thia-4-oxopentyl)benzene, 1-(2-triethoxysilylethyl)-3,5-bis-(3-thia-4-oxohexyl) benzene, 1-(2-triethoxysilylethyl)-3,5-bis-(3-thia-4-oxoheptyl)benzene, 1-(2-tripropoxysilylmethyl)-3,5-bis-(3-thia-4-oxopentyl)benzene, 4-(2-triethoxysilylethyl)-1,2-bis-(2-thia-3-oxopentyl)benzene, 1-(2-diethoxymethylsilylethyl)-3,5-bis-(3-thia-4-oxopentyl)benzene, 4-(2-dimethylethoxysilylethyl)-1,2-bis-(3-thia-4-oxopentyl) benzene, 4-(4-triethoxysilyl-1-oxa-butyl)-1,2-bis-(3-thia-4-oxopentyl)benzene, 4-(2-triethoxysilylethyl)-1,2-bis-(2-thia-3-oxopentyl)cyclohexane, 1-(2-triethoxysilylethyl)-2,4-bis-(2-thia-3-oxopentyl)cyclohexane, 2-(2-triethoxysilylethyl)-1,4-bis-(2-thia-3-oxopentyl) cyclohexane, 4-(2-diethoxymethylsilylethyl)-1,2-bis-(3-thia-4-oxopentyl)cyclohexane, 4-(2-dimethylethoxysilylethyl)-1,2-bis-(3-thia-4-oxopentyl) cyclohexane, 4-(2-triethoxysilylethyl)-1,2-bis-(3-thia-4-oxohexyl)cyclohexane, 1-(2-triethoxysilylethyl)-2,4-bis-(3-thia-4-oxohexyl)cyclohexane, 2-(2-triethoxysilylethyl)-1,4-bis-(3-thia-4-oxohexyl)cyclohexane, 4-(2-triethoxysilylethyl)-1,2-bis-(3-thia-4-oxononyl) cyclohexane, 1-(2-triethoxysilylethyl)-2,4-bis-(3-thia-4-oxononyl)cyclohexane, 2-(2-triethoxysilylethyl)-1,4-bis-(3-thia-4-oxononyl)cyclohexane, 4-(2-triethoxysilylethyl)-1,2-bis-(3-thia-4-oxoundecyl)cyclohexane, 1-(2-triethoxysilylethyl)-2,4-bis-(3-thia-4-oxoundecyl) cyclohexane, 2-(2-triethoxysilylethyl)-1,4-bis-(3-thia-4-oxoundecyl)cyclohexane, 4-(2-dimethylethoxysilylethyl)-1,2-bis-(3-thia-4-oxododecyl)cyclohexane, 4-(2-triethoxysilylethyl)-1,2-bis-(3-thia-4-oxododecyl) cyclohexane, 1-(2-triethoxysilylethyl)-3,5-bis-(3-thia-4-oxopentyl)mesitylene and 4-(6-triethoxysilyl-3-thiahexyl)-1,2-bis-(3-thia-4-oxopentyl)cyclohexane, and mixtures thereof.

Representative examples of blocked mercaptosilane (iv) of the present invention include, but are not limited to, triethoxysilylmethyl thioformate, 2-triethoxysilylethyl thioacetate, 3-triethoxysilylpropyl thiopropanoate, 3-triethoxysilylpropyl thiohexanoate, 3-triethoxysilylpropyl thiooctanoate, 3-diethoxymethylsilylpropyl thiooctanoate, 3-ethoxydimethylsilylpropyl thiooctanoate, 3-triethoxysilylpropyl thiododecanoate, 3-triethoxysilylpropyl thiooctadecanoate, 3-trimethoxysilylpropyl thiooctanoate, 3-triacetoxysilylpropyl thioacetate, 3-dipropoxymethylsilylpropyl thiopropanoate, 4-oxa-hexyloxydimethylsilylpropyl thiooctanoate, and mixtures thereof.

The silane, if liquid, may be loaded on a carrier, such as a porous polymer, carbon black, siliceous filler or silica so that it is in solid form for delivery to the rubber. As previously stated, the silane can react with the surface hydroxyl groups of the siliceous filler or silica, especially lithe silane and filler mixture is heated to about 50 to 150° C. at atmospheric or reduced pressure.

The amount of blocked mercaptosilane (iii) in the mixture of blocked mercaptosilanes (iii) and (iv) can range from 5 to 50 weight percent based upon the total weight of the mixture, more particularly from 10 to 40 weight percent based upon the total weight of the mixture and most particularly from 15 to 35 weight percent based upon the total weight of the mixture.

Blocked mercaptosilanes (iii) and (iv) are mixed with the vulcanizable rubber (organic polymer) component(s) (i) before, during, or after the compounding of filler(s) (ii) with the latter. In a preferred embodiment, blocked mercaptosilanes (iii) and (iv) are added before or during the compounding of the filler(s) into the rubber(s) since these silanes tend to facilitate and improve the dispersion of the filler(s). The total amount of blocked mercaptosilanes (iii) and (iv) present in the resulting combination can range from 0.05 to 25 parts by weight per hundred parts by weight of rubber(s) (phr), more particularly from 0.2 to 12 phr and most particularly from 1 to 8 phr mixed with the rubber (organic polymer) component(s). Filler(s) can be used in quantities ranging from 5 to 140 phr, more particularly from 25 to 110 phr.

Optional Deblocking Agent (v)

When reaction of the mixture of blocked mercaptosilanes (iii) and (iv) to couple the filler(s) to the polymer(s) is desired, at least one acyl group-reactive deblocking agent (v) will also be present in the rubber composition.

Acyl group-reactive deblocking agent(s) (v) may be added in quantities ranging from 0.05 to 20 phr, more particularly in the range of 0.1 to 5 phr, and most particularly in the range of from 0.5 to 3 phr. If alcohol or water is present (as is common) in the mixture, a catalyst (e.g., tertiary amines, Lewis acids, or thiols) may be used to initiate and promote the release of the blocking groups by hydrolysis or alcoholysis thus liberating the corresponding active mercaptosilanes. Alternatively, acyl-deblocking agent (v) may be a nucleophile containing a hydrogen atom sufficiently labile such that the hydrogen atom will be transferred to the site of the original blocking group to provide the corresponding active mercaptosilane. Thus, with a blocking group acceptor molecule, an exchange of hydrogen from the nucleophile would occur with the blocking groups of blocked mercaptosilanes (iii) and (iv) to form mercaptosilanes and the corresponding derivative of the nucleophile containing the original blocking group. This transfer of the blocking group from the mercaptosilane to the nucleophile can be driven, for example, by the greater thermodynamic stability of the products (mercaptosilane and nucleophile containing the blocking group) relative to the initial reactants (blocked mercaptosilane and nucleophile). For example, if the nucleophile were an amine containing an N—H bond, transfer of the blocking group from the blocked mercaptosilane would yield the mercaptosilane and an amide corresponding to the acyl group.

What is important is that for the acyl blocking group initially present on the blocked mercaptosilane and the acyl-reactive deblocking agent (v) employed, the initially substantially inactive (from the standpoint of coupling to the organic polymer) blocked mercaptosilane is substantially converted at the desired point in the rubber compounding procedure to the active mercaptosilane. It is noted that partial amounts of the nucleophile may be used (i.e., a stoichiometric deficiency) if one were to deblock only part of the blocked mercaptosilane to control the degree of vulcanization of a specific formulation.

Water typically is present on the filler as a hydrate or bound to the filler in the form of a hydroxyl group. Acyl-reactive deblocking agent (v) can be added in the curative package or, alternatively, at any other stage in the compounding process as a single component.

In one embodiment, acyl-reactive deblocking agent (v) is of the formula:

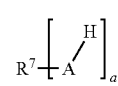

wherein:

$R^7$ is a monovalent or polyvalent organic radical containing from 1 to 30 carbon atoms or hydrogen, each occurrence of A is independently an oxygen, sulfur or —NR$^8$ group, where each occurrence of R$^8$ is independently a monovalent or polyvalent organic radical containing from 1 to 30 carbon atoms or hydrogen; and, the subscript a in an integer of from 1 to 100.

More particularly, each occurrence of R$^7$ and R$^8$ is independently hydrogen or a group derived from a hydrocarbon containing from 1 to 30 carbon atoms obtained by removing one or more hydrogen atoms and, optionally, contains at least one heteroatom selected from the group consisting of oxygen, nitrogen, sulfur and phosphorus.

Examples of acyl-reactive deblocking agents (v) in accordance with the foregoing formula include water or monoalcohols or glycols or polyols, any primary or secondary amines or amines containing C═N double bonds such as imines or guanidines with the proviso that said amine contain at least one N—H (nitrogen-hydrogen) bond. Numerous specific examples of such guanidines, amines and imines are well known in the art as components of rubber, e.g., those disclosed in J. Van Alphen, *Rubber Chemicals*, (Plastics and Rubber Research institute TNO, Delft, Holland, 1973). Some examples include N,N'-diphenylguanidine, N,N',N''-triphenylguanidine, N,N'-di-ortho-tolylguanidine, orthobiguanide, hexamethylenetetramine, cyclohexylethylamine, dibutylamine and 4,4'-diaminodiphenylmethane. Any general acid catalyst used to transesterify esters, such as Brönsted or Lewis acids, can be used as catalyst.

Other Optional Components (vi)

The rubber composition herein can be compounded with one or more other optional components, or additives, (vi) known in the rubber compounding art. Examples of such additives include the aforementioned inert particulate fillers, curing aids such as sulfur, activators, retarders and accelerators, processing additives such as oils, resins including tackifying resins, silicas, plasticizers, fillers, pigments, fatty acids, zinc oxide, waxes, antioxidants and antiozonants, peptizing agents and reinforcing materials such as, for example, carbon black. Depending on the intended use of the vulcanizable and vulcanized rubber compositions, the aforementioned additives are typically utilized in known or conventional amounts.

Vulcanization of the vulcanizable component(s) present in the rubber composition herein can be conducted in the presence of one or more sulfur-containing vulcanization agents (in addition to unblocked mercaptosilanes (iii) and (iv)) examples of which include elemental sulfur (free sulfur) or sulfur-donating vulcanization agents, for example, amino disulfides, polymeric polysulfides and sulfur olefin adducts and/or non-sulfur type vulcanization agents such asperoxides. The selected vulcanization agent(s) is/are conventionally added in the final, or productive, rubber composition mixing step. The vulcanization agents can be added in the productive mixing stage in amounts ranging from 0.1 to 3 phr, or even in some circumstances up to about 8 phr, with a range of from 0.2 to 2.5 phr and in some cases, from 0.5 to 2.5 phr, being preferred.

Vulcanization accelerators, e.g., sulfur donors, can be used herein. Representative examples include benzothiazoles, alkyl thiuram disulfides, guanidine derivatives and thiocarbamates. Specific accelerators of the foregoing and other types include, but are not limited to, mercapto benzothiazole, tetramethyl thiuram disulfide, benzothiazole disulfide, diphenylguanidine, zinc dithiocarbamate, alkylphenoldisulfide, zinc butyl xanthate, N-dicyclohexyl-2-benzothiazolesulfenamide, N-cyclohexyl-2-benzothiazolesulfenamide, N-oxydiethylenebenzothiazole-2-sulfenamide, N,N-diphenylthiourea, dithiocarbamylsulfenamide, N,N-diisopropylbenzothiozole-2-sulfenamide, zinc-2-mercaptotoluimidazole, dithiobis(N-methyl piperazine), dithiobis(N-beta-hydroxy ethyl piperazine) and dithiobis(dibenzyl amine). Other useful sulfur donors, include, for example, thiuram and morpholine derivatives. Representative of such donors are, for example, but not limited to, dimorpholine disulfide, dimorpholine tetrasulfide, tetramethyl thiuram tetrasulfide, benzothiazyl-2,N-dithiomorpholide, thioplasts, dipentamethylenethiuram hexasulfide and disulfidecaprolactam.

Accelerators may be used to control the time and/or temperature required for vulcanization and to improve the properties of the vulcanizate. In one embodiment, a single accelerator system may be used, i.e., a primary accelerator. Conventionally and preferably, a primary accelerator(s) is/are used in total amounts ranging from 0.5 to 4 phr, preferably 0.8 to 1.5 phr. Combinations of a primary and a secondary accelerator may be used with the secondary accelerator being used in smaller amounts (e.g., 0.05 to 3 phr) in order to activate and to improve the properties of the vulcanizate. Delayed action accelerators and/or vulcanization retarders may also be used. Suitable types of accelerators include amines, disulfides, guanidines, thioureas, thiazoles, thiurams, sulfenamides, dithiocarbamates and xanthates. Preferably, the primary accelerator is a sulfenamide. If a second accelerator is used, the secondary accelerator is preferably a guanidine, dithiocarbamate or thiuram compound.

Typical amounts of tackifier resins, if used, are 0.5 to 10 phr, usually 1 to 5 phr. Typical amounts of processing aids are 1 to 50 phr. Such processing aids include, for example, aromatic, naphthenic and/or paraffinic processing oils. Typical amounts of antioxidants are 1 to 5 phr. Representative antioxidants may be, for example, diphenyl-p-phenylenediamine and others such as those disclosed in the *Vanderbilt Rubber Handbook* (1978), pages 344-46. Typical amounts of antiozonants comprise 1 to 5 phr. Typical amounts of fatty acids, which, if used, can include stearic acid, are 0.5 to 3 phr. Typical amounts of zinc oxide are 2 to 5 phr. Typical amounts of waxes are 1 to 5 phr. Often microcrystalline waxes are used. Typical amounts of peptizers are 0.1 to 1 phr. Typical peptizers may, for example, be pentachlorothiophenol and dibenzamidodiphenyl disulfide.

Addition of an alkyl silane to the coupling agent system (blocked mercaptosilanes (iii) and (iv)) plus additional free sulfur source and/or vulcanization accelerator, typically in a mole ratio of alkyl silane to the total of the blocked mercaptosilanes (iii) and (iv) in a range of from 1/50 to 1/2; promotes an even better control of rubber composition processing and aging.

Silane-Reactive Particulate Filler (ii) Pre-Reacted with a Mixture of Blocked Mercaptosilanes (iii) and (iv)

It is also within the scope of the present invention to provide at least a portion up to the full amount of silane-reactive particulate filler (ii) pre-reacted with a mixture of at least a portion up to the full amount of blocked mercaptosilane (iii) and at least a portion up to the full amount of blocked mercaptosilane (iv), the amounts of silane-reactive particulate filler (ii) and blocked mercaptosilanes (iii) and (iv) replacing like amounts of these components in the aforedescribed rubber composition. Therefore, the invention includes the following additional embodiments:

(1) a particulate-filled rubber composition comprising components (i), part of (ii), part of (iii), part of (iv) and the remainder of (ii) pre-reacted with a mixture of the remainder of (iii) and the remainder of (iv);

(2) a particulate-filled rubber composition comprising components (i), part of (ii), part of (iv) and the remainder of (ii) pre-reacted with a mixture of all of (iii) and the remainder of (iv);

(3) a particulate-filled rubber composition comprising components (i), part of (ii), part of (iii) and the remainder of (ii) pre-reacted with a mixture of the remainder of (iii) and all of (iv);

(4) a particulate-filled rubber composition comprising components (i), part of (iii), part of (iv) and all of (ii) pre-reacted with a mixture of the remainder of (iii) and the remainder of (iv);

(5) a particulate-filled rubber composition comprising components (i), part of (iv) and all of (ii) pre-reacted with a mixture of all of (iii) and the remainder of (iv);

(6) a particulate-filled rubber composition comprising (i), part of (iii) and all of (ii) pre-reacted with a mixture of the remainder of (iii) and all of (iv); and, (7) a particulate-filled rubber composition comprising (i) and all of (ii) pre-reacted with a mixture of all of (iii) and all of (iv).

Process for Making the Particulate-Filled Rubber Composition

In practice, sulfur-vulcanized rubber articles are typically prepared by thermomechanically mixing rubber and various ingredients in a sequentially stepwise manner followed by shaping and curing the compounded rubber to form a vulcanized product. First, for the aforesaid mixing of the rubber and various ingredients, typically exclusive of vulcanizing agents and vulcanization accelerators (collectively "curing agents"), the rubber(s) and various rubber compounding ingredients typically are blended in at least one, and often (in the case of silica-filled low rolling resistance tires) two, preparatory thermomechanical mixing stage(s) in suitable mixers. Such preparatory mixing is referred to as nonproductive mixing or nonproductive mixing steps or stages. Such preparatory mixing usually is conducted at temperatures of up to 100° to 200° C. and often up to 140° to 180° C. Subsequent to such preparatory mix stages, in a final mixing stage, sometimes referred to as a productive mixing stage, acyl-reactive deblocking agent(s) (in the case of this invention), curing agent(s), and possibly one or more additional ingredients are mixed with the rubber composition, typically at a temperature within a range of from 50° to 130° C., which is a lower temperature than the temperatures utilized in the preparatory mix stages to prevent or retard premature curing of the curable rubber, sometimes referred to as scorching. The rubber mixture, variously referred to as a rubber compound or rubber composition, is typically allowed to cool, sometimes during or after a process intermediate mill mixing carried out between the aforesaid various mixing steps, for example, to a temperature of about 50° C. or lower. When it is desired to mold and to cure the rubber, the rubber is placed into the appropriate mold at about at least 130° C. and up to about 200° C., causing the vulcanization of the rubber by the mercapto groups on the unblocked mercaptosilanes and any other vulcanizing agent(s), e.g., free sulfur source(s) that may be present in the rubber mixture.

By thermomechanical mixing, it is meant that the rubber compound, or composition of rubber and rubber compounding ingredients, is mixed in a rubber mixer under high shear conditions where it autogeneously heats up as a result of the mixing primarily due to shear and associated friction within the rubber mixture in the rubber mixer. Several chemical reactions may occur at various steps in the mixing and curing processes.

The first reaction is a relatively fast reaction and may be considered to take place between the filler and the $SiX_3$ group of blocked mercaptosilanes (iii) and (iv). Such reaction may occur at a relatively low temperature such as, for example, at about 120° C. The second and third reactions may be considered herein to be the deblocking of the mercaptosilane and the subsequent reaction which takes place between the sulfuric part of the organosilane (after deblocking) and the sulfur-vulcanizable rubber(s) at a higher temperature, for example, above about 140° C.

Another sulfur source may be used, for example, in the form of elemental sulfur as $S_8$. A sulfur donor is considered herein as a sulfur containing compound which liberates free, or elemental, sulfur at a temperature in a range of 140° to 190° C. Examples of such sulfur donors may be, but are not limited to, polysulfide vulcanization accelerators and organosilane polysulfides with at least two connecting sulfur atoms in its polysulfide bridge. The amount of free sulfur source addition to the mixture can be controlled or manipulated as a matter of choice relatively independently from the addition of the aforesaid blocked mercaptosilane. Thus, for example, the independent addition of a sulfur source may be manipulated by the amount of addition thereof and by sequence of addition relative to addition of other ingredients to the rubber mixture.

In one embodiment of the present invention, a rubber composition is prepared by the process which comprises:

a) thermomechanically mixing, in at least one preparatory mixing step, to a first elevated temperature, e.g., from 140° to 200° C. and preferably from 160° to 190° C., for a suitable period, e.g., from 20 minutes and preferably from 4 to 15 minutes:

at least one sulfur vulcanizable rubber (i), e.g., 100 parts by weight thereof, advantageously selected from conjugated diene homopolymers and copolymers and copolymers of at least one conjugated diene and aromatic vinyl compound, at least one silane-reactive particulate filler (ii), e.g., from 5 to 140 phr (parts by weight per hundred parts by weight rubber), preferably 25 to 110 phr, or a mixture of silane-reactive particulate filler(s) (ii) and inert particulate filler(s), e.g., 15 to 99 weight percent silane-reactive particulate filler(s) and, correspondingly, from 1 to 85 weight percent inert particulate filler(s) based upon the combined weights of the silane-reactive and inert particulate fillers, mixture of at least one blocked mercaptosilane (iii) and at least one blocked mercaptosilane (iv), e.g., in a total amount of said mixture of from 0.05 to 25 phr;

wherein blocked mercaptosilane (iii) has the formula:

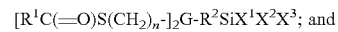

[R$^1$C(=O)S(CH$_2$)$_n$-]$_2$G-R$^2$SiX$^1$X$^2$X$^3$; and blocked mercaptosilane (iv) has the formula:

R$^3$C(=O)SR$^4$SiX$^1$X$^2$X$^3$;

R$^1$, each occurrence, is independently hydrogen or a monovalent hydrocarbon group containing up to 12 carbon atoms;

R$^2$ is a divalent hydrocarbon group containing up to 10 carbon atoms and, optionally, an oxygen atom or sulfur atom;

R$^3$ is hydrogen or a monovalent hydrocarbon group containing up to 18 carbon atoms;

R$^4$ is a divalent hydrocarbon group containing up to 12 carbon atoms;

G is a trivalent cyclic hydrocarbon group containing up to 10 carbon atoms;

$X^1$, each occurrence, is independently selected from the group consisting of hydrogen, $R^5O$— and $R^5C(\!\!=\!\!O)O$—, wherein $R^5$ is hydrogen or a monovalent hydrocarbon group containing up to 18 carbon atoms and, optionally, at least one oxygen atom;

$X^2$ and $X^3$, each occurrence, is independently chosen from the group consisting of the members listed for $R^6$ and $X^1$, wherein $R^6$ is a monovalent hydrocarbon group of up to 6 carbon atoms; and, n is an integer from 1 to 5;

b) blending the mixture resulting from (a), in a final thermomechanical mixing step, at a second elevated temperature which is less than the first elevated temperature, e.g., from 50° to 130° C., for a suitable period, e.g., from up to 30 minutes and preferably from 1 to 3 minutes, at least one acyl-reactive deblocking agent, preferably at from 0.05 to 20 phr, and, optionally, at least one vulcanization agent at from 0.1 to 8 phr; and, optionally, c) curing said mixture at a third elevated temperature, e.g., from 130° to 200° C., for a suitable period, e.g., from 5 to 60 minutes.

The invention also includes as one of its embodiments a free-flowing filler composition obtained by reacting silane-reactive particulate filler (ii) with a mixture of blocked mercaptosilane (iii) and blocked mercaptosilane (iv). If desired, the aforesaid free-flowing composition can be combined with one or more components of the rubber composition of the invention, e.g., at least one vulcanizable rubber (i).

In another embodiment of the present invention, the foregoing process may also comprise the additional steps of preparing an assembly of a tire or vulcanizable rubber with a tread comprised of the rubber composition prepared according to this invention and vulcanizing the assembly at a temperature within the range of 130° to 200° C.

In yet another embodiment of the present invention, the rubber composition of this invention can be used for the fabrication of a variety of articles. For example, it can be used for various tire compounds such as tread, sidewall, bead and the like. Such tires can be built, shaped, molded and cured by various methods which are known and will be readily apparent to those having skill in such art. Others include hoses, belts, rollers, insulation jacketing, industrial goods, shoe soles, bushings, damping pads, and the like.

The invention may be better understood by reference to the following examples in which the parts and percentages are by weight unless otherwise indicated.

EXAMPLE 1

Preparation of
3-(octanoylthio)-1-propyltriethoxysilane (Silane 1)

Into a 12-liter, three-necked round bottom flask equipped with mechanical stirrer, addition funnel, thermocouple, heating mantle, $N_2$ inlet, and temperature controller were charged 3-mercaptopropyltriethoxysilane (1,021 grams, 3.73 moles purchase as SILQUEST® A-1891 silane from Momentive Performance Materials, Inc.), triethylamine (433 grams), and hexane (3,000 ml). The solution was cooled in an ice bath, and octanoyl chloride (693 grams, 4.25 moles) were added over a two hour period via the addition funnel. After addition of the acid chloride was complete, the mixture was filtered two times, first through a 0.1 µm filter and then through a 0.01 µm filter, using a pressure filter, to remove the salt. The solvent was removed under vacuum. The remaining yellow liquid was vacuum distilled to yield 1,349 grams of octanoylthiopropyltriethoxysilane as a clear, very light yellow liquid. The yield was 87 percent.

EXAMPLE 2

Preparation of (2-triethoxysilylethyl)-bis-(3-thia-4-oxohexyl)cyclohexane (Silane 2)

This example illustrates the preparation of a thiocarboxylate alkoxysilane from a silane containing two vinyl groups through the formation of an intermediate thioacetate silane.

The preparation of the (2-trimethoxysilylethyl)divinylcyclohexane was prepared by hydrosilation. Into a 5 L, three-neck round bottomed flask equipped with magnetic stir bar, temperature probe/controller, heating mantle, addition funnel, condenser, and air inlet were charged trivinylcyclohexane (2,001.1 grams, 12.3 moles) and VCAT catalysts (1.96 grams, 0.01534 gram platinum). Air was bubbled into the vinyl silane by means of the air inlet where the tube was below the surface of the silane. The reaction mixture was heated to 110° C. and the trimethoxysilane (1,204 grams, 9.9 moles) was added over a 3.5 hour period. The temperature of the reaction mixture increased to a maximum value of 130° C. The reaction mixture was cooled to room temperature and 1,3,5-trimethyl-2,4,6-tris(3,5-di-tert-butyl-4-hydroxybenzyl)benzene (3 grams, 0.004 mole) was added. The reaction mixture was distilled at 122° C. and 1 mmHg pressure to give 1,427 grams of (2-trimethoxysilylethyl)divinylcyclohexane. The yield was 51 percent.

The (2-triethoxysilylethyl)divinylcyclohexane was prepared by transesterification. Into a 3 L, three-neck round bottomed flask equipped with magnetic stir bar, temperature probe/controller, heating mantle, addition funnel, distilling head and condenser, and nitrogen inlet were charged (2-trimethoxysilylethyl)divinylcyclohexane (284 grams, 2.33 moles), sodium ethoxide in ethanol (49 grams of 21% sodium ethoxide, purchased from Aldrich Chemical) and ethanol (777 grams, 16.9 moles). The reaction mixture was heated and the methanol and ethanol were removed by distillation at atmospheric pressure. The crude product was then distilled at 106° C. and under reduced pressure of 0.4 mmHg to give 675 grams of product, 89 percent yield.

The (2-triethoxysilylethyl)bis-(3-thia-4-oxopentyl)cyclohexane was prepared by addition of thioacetic acid to the divinylsilane. Into a 1 L, three-neck round bottomed flask equipped with magnetic stir bar, temperature probe/controller, heating mantle, addition funnel, condenser, air inlet and a sodium hydroxide scrubber, was charged thioacetic acid (210 grams, 2.71 moles). The (2-triethoxysilylethyl)divinylcyclohexane (400 grams, 1.23 moles) was added slowly over a period of 30 minutes and at room temperature by means of an addition funnel. The reaction was an exothermic reaction. The temperature of the mixture increased to 94.6° C. The mixture was stirred for 2.5 hours and allowed to cool to 38.8° C. Additional thioacetic acid (10 grams, 0.13 moles) was added and a slight exothermal reaction was observed. The reaction mixture was stirred overnight (18 hours) at about 25° C. Analysis indicated that the reaction mixture contained less than 2 percent thioacetic acid. Its overall purity was 91 percent. The reaction mixture was further purified by a distillation using a Kugel apparatus under reduced pressure.

The dimercaptosilane intermediate, (2-triethoxysilylethyl)bis(2-mercaptoethyl)cyclohexane, was prepared by removing the acetyl groups from (2-triethoxysilylethyl)bis-(3-thia-4-oxopentyl)cyclohexane. Into a 5 L, three-neck round bottomed flask equipped with magnetic stir bar, temperature probe/controller, heating mantle, addition funnel, distilling head and condenser, 10-plate Oldershaw column and nitrogen inlet were charged (2-triethoxysilylethyl) bis-(3-thia-4-oxopentyl)cyclohexane (2,000 grams, 4.1 moles), ethanol (546.8 grams, 11.8 moles) and sodium ethoxide in ethanol (108 grams of a 21% sodium ethoxide in ethanol). The pH of the reaction mixture was about 8. The reaction mixture was heated to 88° C. for 24 hours to remove the ethyl acetate and ethanol from the reaction mixture. Twice ethanol (1 liter) was added to the mixture and the pH of the reaction mixture was increase to about 10 by the addition of 21% sodium ethoxide in ethanol (21 grams) and heated an additional 6.5 hours. The reaction mixture was cooled and then pressure filtered. The reaction mixture was stripped at a temperature less than 95° C. and 1 mmHg pressure. The stripped product was filtered to give (2-triethoxysilylethyl)bis(2-mercaptoethyl)cyclohexane (1398 grams, 3.5 moles, 86% yield).

The (2-triethoxysilylethyl)-bis-(3-thia-4-oxohexyl)cyclohexane was prepared by the acetylation of the bismercaptosilane. Into a 5 L, three-neck round bottomed flask equipped with magnetic stir bar, temperature probe/controller, ice/water bath, addition funnel and condenser were charged (2-triethoxysilylethyl)bis(2-mercaptoethyl)cyclohexane (1010.6 grams, 2.56 moles), triethylamine (700 grams, 6.93 moles) and methylene chloride (1000 grams). Propionyl chloride (473.8 grams, 5.12 moles) was added to the stirred reaction mixture over a 1.5 hour period. The reaction mixture temperature increased to 50° C. Additional propionyl chloride (45.4 grams, 0.49 mole) was added. The reaction mixture was filtered and the salts were mixed with 500 mL of methylene chloride and washed with three times with distilled water and twice with saturated sodium chloride solution. The organic phase was dried over anhydrous magnesium sulfate and then stripped at 124° C. and reduced pressure to remove the volatile components. The stripped product (1196 grams, 2.36 moles) was analyzed by GC/MS, NMR and LC and the yield was 92 percent.

EXAMPLE 3

Preparation of (2-triethoxysilylethyl)-bis-(3-thia-4-oxopentyl)cyclohexane (Silane 3)

This example illustrates the preparation of a thiocarboxylate alkoxysilane from a silane containing two vinyl groups through the reaction with thioacetate silane.

The preparation of the (2-trimethoxysilylethyl)divinylcyclohexane was prepared by hydrosilation. Into a 5 L, three-neck round bottomed flask equipped with magnetic stir bar, temperature probe/controller, heating mantle, addition funnel, condenser, and air inlet were charged trivinylcyclohexane (2,001.1 grams, 12.3 moles) and VCAT catalysts (1.96 grams, 0.01534 gram platinum). Air was bubbled into the vinyl silane by means of the air inlet where the tube was below the surface of the silane. The reaction mixture was heated to 110° C. and the trimethoxysilane (1,204 grams, 9.9 moles) was added over a 3.5 hour period. The temperature of the reaction mixture increased to a maximum value of 130° C. The reaction mixture was cooled to room temperature and 1,3,5-trimethyl-2,4,6-tris(3,5-di-tert-butyl-4-hydroxylbenzyl)benzene (3 grams, 0.004 mole) was added. The reaction mixture was distilled at 122° C. and 1 mmHg pressure to give 1,427 grams of (2-trimethoxysilylethyl) divinylcyclohexane. The yield was 51 percent.

The (2-triethoxysilylethyl)divinylcyclohexane was prepared by transesterification. Into a 3 L, three-neck round bottomed flask equipped with magnetic stir bar, temperature probe/controller, heating mantle, addition funnel, distilling head and condenser, and nitrogen inlet were charged (2-trimethoxysilylethyl)divinylcyclohexane (284 grams, 2.33 moles), sodium ethoxide in ethanol (49 grams of 21% sodium ethoxide, purchased from Aldrich Chemical) and ethanol (0.777 grams, 16.9 moles). The reaction mixture was heated and the methanol and ethanol were removed by distillation at atmospheric pressure. The crude product was then distilled at 106° C. and under reduced pressure of 0.4 mmHg to give 675 grams of product, 89 percent yield.

The (2-triethoxysilylethyl)bis-(3-thia-4-oxopentyl)cyclohexane was prepared by addition of thioacetic acid to the divinylsilane. Into a 1 L, three-neck round bottomed flask equipped with magnetic stir bar, temperature probe/controller, heating mantle, addition funnel, condenser, air inlet and a sodium hydroxide scrubber, was charged thioacetic acid (210 grams, 2.71 moles). The (2-triethoxysilylethyl)divinylcyclohexane (400 grams, 1.23 moles) was added slowly over a period of 30 minutes and at room temperature by means of an addition funnel. The reaction was an exothermic reaction. The temperature of the mixture increased to 94.6° C. The mixture was stirred for 2.5 hours and allowed to cool to 38.8° C. Additional thioacetic acid (10 grams, 0.13 moles) was added and a slight exothermal reaction was observed. The reaction mixture was stirred overnight (18 hours) at about 25° C. Analysis indicated that the reaction mixture contained less than 2 percent thioacetic acid. Its overall purity was 91 percent. The reaction mixture was further purified by a distillation using a Kugel apparatus under reduced pressure.

Comparative Examples A-C, Examples 4-11

The Use of Silanes 1-3 in Low Rolling Resistant Tire Tread Formulation

A model low rolling resistance passenger tire tread formulation as described in Table 1 and a mix procedure employed with Silanes 1, 2 or 3 or with mixtures of Silane 1 and Silane 2 or Silane 1 and Silane 3, and hereinafter described specifically for Silane 1 were used to evaluate representative examples of the silanes of the present invention.

Silane 1 of Example 1 was mixed as follows in a "B" BANBURY® (Farrell Corp.) mixer with a 103 cu. in. (1690 cc) chamber volume. The mixing of the rubber was done in two steps. The mixer was turned on with the mixer at 80 rpm and the cooling water at 71° C. The rubber polymers were added to the mixer and ram down mixed for 30 seconds. The silica and the other ingredients in Masterbatch 1 of Table 1 except for the silane and the oils were added to the mixer and ram down mixed for 60 seconds. The mixer speed was reduced to 35 rpm and then the silane and oils of the Masterbatch 1 were added to the mixer and ram down for 60 seconds. The mixer throat was dusted down and the ingredients ram down mixed until the temperature reached 149° C. The ingredients were then mixed for an addition 3 minutes and 30 seconds. The mixer speed was adjusted to hold the temperature between 152 and 157° C. The rubber was dumped (removed from the mixer), a sheet was formed on a roll mill set at about 85° to 88° C., and then allowed to cool to ambient temperature.

In the second step, Masterbatch 1 was recharged into the mixer. The mixer's speed was 80 rpm, the cooling water was set at 71° C. and the batch pressure was set at 6 MPa. The Masterbatch 1 was ram down mixed for 30 seconds and then the temperature of the Masterbatch 1 was brought up to 149° C., and then the mixer's speed was reduce to 32 rpm. The zinc oxide and stearic acid were added (Masterbatch 2) and the rubber was mixed for 3 minutes and 20 seconds at temperatures between 152 and 157° C. After mixing, the rubber was dumped (removed from the mixer), a sheet was formed on a roll mill set at about 85° to 88° C., and then allowed to cool to ambient temperature.

The rubber masterbatch and the curatives were mixed in an instrumented "OOC." BANBURY® (Farrell Corp.) mixer with 158 cu. In. (2,600 cc) chamber volume. The mixing of the rubber was done in three steps. The mixer was turned on with the mixer at 80 rpm and the cooling water at 70° C. The rubber polymers were added to the mixer and ram down mixed for 30 seconds. The silica and the silane were added to the mixer and ram down mixed for 30 seconds. The other ingredients in Masterbatch 1 except for the oils were added to the mixer and ram down mixed for 60 seconds. The mixer speed was reduced to 65 rpm and then the oils of Masterbatch 1 were added to the mixer and ram down mixed for 60 seconds. The mixer throat was dusted down and the ingredients ram down mixed until the temperature reached 150° C. The ingredients were then mixed for an additional 3 minutes and 30 seconds. The mixer speed was adjusted to hold the temperature between 150 and 155° C. The rubber was dumped (removed from the mixer); a sheet was formed on the roll mill set at about 85° to 90° C., and then allowed to cool to ambient temperature.

In the second step, Masterbatch 1 was recharged into the mixer. The mixer's speed was 80 rpm, the cooling water was set at 70° C., and the ram pressure was set at 25 psi. Masterbatch 2 was ram down mixed for 150 seconds while the temperature of the Masterbatch was brought up to 150° C., and then the mixer's speed was reduced to 50 rpm and the rubber was mixed for 40 seconds at temperatures between 150 and 155° C. After mixing, the rubber was dumped (removed from the mixer), a sheet was formed on the roll mill set at about 85° to 90° C., and then allowed to cool to ambient temperature.

In the third step, the mixer speed was set to 50 rpm, the cooling water was set at 70° C., and the ram pressure was set at 25 psi. The rubber Masterbatch 2 and the curatives were ram down mixed for 180 seconds while the temperature of the Final Mix was brought up to 110° C. After mixing, the rubber was dumped (removed from the mixer), a sheet was formed on the roll mill set at about 85° to 90° C., and then allowed to cool to ambient temperature. The curing condition was the rubber was dumped (removed from the mixer), a sheet was formed on the roll mill set at about 85° to 90° C., and then allowed to cool to ambient temperature. The curing condition was 160° C. for 20 minutes.

The performance data for individual Silanes 1, 2 and –3, labeled as Comparative Examples A, B and C, respectively, and for mixtures of Silanes 1 and 2 and Silanes 1 and 3, are provided in Tables 1, 2 and 3. The test procedures for evaluating the vulcanized (cured) rubber compositions herein are described in the following ASTM methods:

| | |
|---|---|
| Mooney Scorch | ASTM D1646 |
| Mooney Viscosity | ASTM D1646 |
| Rheometer (MDR2000) | DIN 53529 |
| Storage Modulus, Loss Modulus, Tensile and Elongation | DIN 53504-R1 |
| DIN Abrasion | DIN Procedure 53516 |
| Heat Buildup | ASTM D623 |
| Percent Permanent Set | ASTM D623 |
| Shore A Hardness | DIN 53505 |
| Fatigue-to-Failure LTA | ASTM D4482 |
| DeMattia Crack Growth | ASTM D813 |
| Rebound | DIN 53512, ASTM D1054 |

Silanes 2 and 3 and mixtures of Silanes 1 and 2 and Silanes 1 and 3 were used to prepare the rubber compositions described in Table 1. The results of the foregoing test procedures are set forth in Tables 2 and 3, infra.

TABLE 1

Formulations of Vulanized Rubber Compositions Containing Silanes and Mixtures Thereof

| Example No. | Comp. Ex. A | Comp. Ex. B | Comp. Ex. C | Ex. 4 | Ex. 5 | Ex. 6 | Ex. 7 | Ex. 8 | Ex. 9 | Ex. 10 | Ex. 11 |
|---|---|---|---|---|---|---|---|---|---|---|---|
| Buna VSL 5025-1, oil extended SBR | 103.2 | 103.2 | 103.2 | 103.2 | 103.2 | 103.2 | 103.2 | 103.2 | 103.2 | 103.2 | 103.2 |
| Buna CB24, polybutadiene | 25.0 | 25.0 | 25.0 | 25.0 | 25.0 | 25.0 | 25.0 | 25.0 | 25.0 | 25.0 | 25.0 |
| Zeosil 1165MP, silica | 85.0 | 85.0 | 85.0 | 85.0 | 85.0 | 85.0 | 85.0 | 85.0 | 85.0 | 85.0 | 85.0 |
| N-330 carbon black | 10.0 | 10.0 | 10.0 | 10.0 | 10.0 | 10.0 | 10.0 | 10.0 | 10.0 | 10.0 | 10.0 |
| Sundex 8125TN, Process oil | 5.0 | 5.0 | 5.0 | 5.0 | 5.0 | 5.0 | 5.0 | 5.0 | 5.0 | 5.0 | 5.0 |
| Flexzone 7P, 6PPD antiozorant | 2.0 | 2.0 | 2.0 | 2.0 | 2.0 | 2.0 | 2.0 | 2.0 | 2.0 | 2.0 | 2.0 |
| Sunproof improved, microcrystalline wax | 1.5 | 1.5 | 1.5 | 1.5 | 1.5 | 1.5 | 1.5 | 1.5 | 1.5 | 1.5 | 1.5 |
| Silane Ex. 1 | 6.800 | | | 6.120 | 5.100 | 4.488 | 3.400 | 6.120 | 5.100 | 4.488 | 3.400 |
| Silane Ex. 2 | | 9.440 | | 0.944 | 2.360 | 3.210 | 4.721 | | | | |
| Silane Ex. 3 | | | 8.920 | | | | | 0.892 | 2.230 | 3.033 | 4.460 |
| Industrene R, stearic acid | 2.0 | 2.0 | 2.0 | 2.0 | 2.0 | 2.0 | 2.0 | 2.0 | 2.0 | 2.0 | 2.0 |
| Non-productive Mix 1 Total | 240.5 | 243.1 | 242.6 | 240.8 | 241.2 | 241.4 | 241.8 | 240.7 | 241.0 | 241.2 | 241.6 |
| Kadox 720 C., ZnO | 2.5 | 2.5 | 2.5 | 2.5 | 2.5 | 2.5 | 2.5 | 2.5 | 2.5 | 2.5 | 2.5 |
| Non-productive Mix 2 Total | 243.0 | 245.6 | 245.1 | 243.3 | 243.7 | 243.9 | 244.3 | 243.2 | 243.5 | 243.7 | 244.1 |
| Rubbermakers 167, sulfur | 2.2 | 2.2 | 2.2 | 2.2 | 2.2 | 2.2 | 2.2 | 2.2 | 2.2 | 2.2 | 2.2 |
| Delac S, CBS | 2.0 | 2.0 | 2.0 | 2.0 | 2.0 | 2.0 | 2.0 | 2.0 | 2.0 | 2.0 | 2.0 |
| DPG | 2.0 | 2.0 | 2.0 | 2.0 | 2.0 | 2.0 | 2.0 | 2.0 | 2.0 | 2.0 | 2.0 |
| Total parts formula | 249.2 | 251.8 | 251.3 | 249.5 | 249.9 | 250.1 | 250.5 | 249.4 | 249.7 | 249.9 | 250.3 |

Tables 2 and 3: Performance Data For Vulcanized Rubber Compositions Containing Silanes 1-3 and Mixtures of Silanes 1 and 2 and 1 and 3

TABLE 2

| | | Comp. Ex. A Silane Ex. 1 | Comp. Ex. B Silane Ex. 2 | Ex. 4 | Ex. 5 | Ex. 6 | Ex. 7 |
|---|---|---|---|---|---|---|---|
| | | | | Weight ratio of Silane Ex. 1/Silane Ex. 2 | | | |
| Ingredients | Units | 100/0 | 0/100 | 90/10 | 75/25 | 66/34 | 50/50 |
| Processing Properties | | | | | | | |
| Mooney Viscosity @ 100° C. | | | | | | | |
| ML(1 + 4) | MU | | | | | | |
| Small Rotor     MB1 | | 87.1 | 83.7 | 86.3 | 85.3 | 85.4 | 87.1 |
| Small Rotor     MB2 | | 56.7 | 69.1 | 57.4 | 62.4 | 62.6 | 69.1 |
| Small Rotor     FM | | 38.2 | 41.9 | 37.8 | 40.2 | 41.2 | 43.7 |
| Mooney Scorch @ 135° C. | | | | | | | |
| Small Rotor     3 pt rise | min | 12.7 | 11.4 | 11.6 | 12.9 | 9.8 | 12.3 |
| Small Rotor     10 pt rise | min | 17.2 | 18.6 | 16.7 | 17.1 | 16.0 | 17.4 |
| MDR @160° C., 30 Mins. | | | | | | | |
| MIN Torque (Mooney Low) | dNm | 2.60 | 2.32 | 2.53 | 2.63 | 2.56 | 2.56 |
| MAX Torque (Mooney High) | dNm | 22.84 | 21.68 | 22.51 | 23.18 | 23.00 | 22.65 |
| Δ Torque | dNm | 20.24 | 19.36 | 19.98 | 20.55 | 20.44 | 20.09 |
| T10 | min | 2.80 | 2.58 | 2.80 | 2.71 | 2.68 | 2.77 |
| T40 | min | 4.45 | 4.32 | 4.39 | 4.32 | 4.29 | 4.47 |
| T90 | min | 17.39 | 15.54 | 17.95 | 18.38 | 17.89 | 17.14 |
| T95 | min | 22.63 | 21.52 | 23.26 | 23.56 | 23.12 | 22.48 |
| Physical Properties | | | | | | | |
| Specific Gravity | g/cm$^3$ | 1.210 | 1.211 | 1.213 | 1.213 | 1.214 | 1.215 |
| 100% Modulus | MPa | 2.9 | 2.9 | 2.9 | 3.0 | 3.1 | 3.2 |
| 300% Modulus | MPa | 13.1 | 13.9 | 13.4 | 13.6 | 13.8 | 14.1 |
| RI (M300/M100) | | 4.5 | 4.8 | 4.6 | 4.5 | 4.5 | 4.4 |
| Tensile | MPa | 14.2 | 16.7 | 15.1 | 15.1 | 15.7 | 15.8 |
| Elongation | % | 349 | 381 | 360 | 358 | 365 | 359 |
| Shore A @ RT | shoreA | 70 | 70 | 70 | 70 | 70 | 72 |
| Shore A @ 70° C. | shoreA | 66 | 67 | 66 | 68 | 68 | 68 |
| Energy @ Break | J/cm$^3$ | 20 | 25 | 21 | 22 | 23 | 23 |
| Graves Tear @ 25° C. | | 41 | 38 | 37 | 40 | 37 | 42 |
| Graves Tear @ 100° C. | | 32 | 33 | 32 | 29 | 36 | 32 |
| Fatigue-to-Failure LTA | KC | 75 | 50 | 54 | 81 | 114 | 42 |
| DeMattia (pierced) Cycles to Fail | KC | 64 | 64 | 128 | 64 | 64 | 128 |
| DIN Abrasion | mm$^3$ | 157 | 154 | 147 | 155 | 147 | 145 |
| Dynamic Properties | | | | | | | |
| Rebound RT | % | 21.0 | 19.0 | 21.4 | 20.5 | 20.7 | 20.1 |
| Rebound 70° C. | % | 45.5 | 42.4 | 43.6 | 42.8 | 42.2 | 41.4 |
| E' max | MPa | 12.3 | 13.5 | 12.9 | 14.6 | 16.1 | 15.4 |
| E' min | MPa | 5.2 | 5.5 | 5.2 | 5.7 | 6.0 | 5.7 |
| E' mean | MPa | 8.5 | 9.2 | 8.7 | 9.7 | 10.4 | 10.1 |
| E* | MPa | 8.2 | 9.1 | 8.5 | 7.8 | 8.7 | 8.7 |
| Tan delta max | | 0.182 | 0.221 | 0.190 | 0.203 | 0.212 | 0.216 |
| Tan delta @ Tg | | 0.775 | 0.725 | 0.761 | 0.777 | 0.748 | 0.752 |
| Tan delta @ 0° C. | | 0.686 | 0.714 | 0.709 | 0.711 | 0.706 | 0.718 |
| Tan delta @ 60° C. | | 0.192 | 0.210 | 0.203 | 0.191 | 0.202 | 0.203 |

TABLE 3

| | | Comp. Ex. A Silane Ex. 1 | Comp. Ex. C Silane Ex. 3 | Ex. 8 | Ex. 9 | Ex. 10 | Ex. 11 |
|---|---|---|---|---|---|---|---|
| | | | | Weight ratio of Silane Ex. 1/Silane Ex. 3 | | | |
| Ingredients | Units | 100/0 | 0/100 | 90/10 | 75/25 | 66/34 | 50/50 |
| Processing Properties | | | | | | | |
| Mooney Viscosity @ 100° C. | | | | | | | |
| ML(1 + 4) | MU | | | | | | |
| Small Rotor     MB1 | | 87.1 | 65.3 | 86.3 | 76.9 | 77.3 | 76.1 |
| Small Rotor     MB2 | | 56.7 | 49.2 | 57.2 | 55.3 | 54.6 | 53.6 |
| Small Rotor     FM | | 38.2 | 37.6 | 37.8 | 38.5 | 39.1 | 38.6 |
| Mooney Scorch @ 135° C. | | | | | | | |
| Small Rotor     3 pt rise | min | 12.7 | 8.8 | 11.0 | 8.2 | 9.6 | 10.0 |
| Small Rotor     10 pt rise | min | 17.2 | 13.4 | 15.4 | 14.4 | 14.6 | 14.2 |

TABLE 3-continued

| | | Comp. Ex. A Silane Ex. 1 | Comp. Ex. C Silane Ex. 3 | Ex. 8 | Ex. 9 | Ex. 10 | Ex. 11 |
|---|---|---|---|---|---|---|---|
| | | | | \multicolumn{4}{c}{Weight ratio of Silane Ex. 1/Silane Ex. 3} |
| Ingredients | Units | 100/0 | 0/100 | 90/10 | 75/25 | 66/34 | 50/50 |
| MDR @160° C., 30 Mins. | | | | | | | |
| MIN Torque (Mooney Low) | dNm | 2.60 | 2.46 | 2.59 | 2.60 | 2.59 | 2.53 |
| MAX Torque (Mooney High) | dNm | 22.84 | 23.91 | 23.33 | 23.32 | 23.46 | 23.78 |
| Δ Torque | dNm | 20.24 | 21.45 | 20.74 | 20.72 | 20.87 | 21.25 |
| T10 | min | 2.80 | 1.93 | 2.60 | 2.52 | 2.41 | 2.23 |
| T40 | min | 4.45 | 3.70 | 4.14 | 4.12 | 4.06 | 3.94 |
| T90 | min | 17.39 | 16.60 | 18.80 | 18.78 | 18.70 | 18.80 |
| T95 | min | 22.63 | 22.05 | 23.94 | 24.05 | 24.00 | 24.00 |
| Physical Properties | | | | | | | |
| Specific Gravity | g/cm$^3$ | 1.210 | 1.207 | 1.212 | 1.213 | 1.213 | 1.216 |
| 100% Modulus | MPa | 2.9 | 2.7 | 2.9 | 2.9 | 2.9 | 2.9 |
| 300% Modulus | MPa | 13.1 | 11.8 | 13.2 | 13.1 | 12.9 | 13.0 |
| RI (M300/M100) | | 4.5 | 4.4 | 4.6 | 4.5 | 4.4 | 4.5 |
| Tensile | MPa | 14.2 | 16.2 | 16.1 | 16.4 | 17.2 | 15.5 |
| Elongation | % | 349 | 423 | 385 | 395 | 416 | 378 |
| Shore A @ RT | shoreA | 70 | 73 | 70 | 70 | 71 | 73 |
| Shore A @ 70° C. | shoreA | 66 | 69 | 67 | 68 | 69 | 70 |
| Energy @ Break | J/cm$^3$ | 20 | 28 | 25 | 26 | 29 | 24 |
| Graves Tear @ 25° C. | | 41 | 39 | 41 | 41 | 38 | 40 |
| Graves Tear @ 100° C. | | 32 | 33 | 33 | 33 | 33 | 34 |
| Fatigue-to-Failure LTA | KC | 75 | 44 | 63 | 70 | 69 | 61 |
| DeMattia (pierced) Cycles to Fail | KC | 64 | 128 | 256 | 64 | 256 | 256 |
| DIN Abrasion | mm$^3$ | 157 | 156 | 157 | 160 | 157 | 162 |
| Dynamic Properties | | | | | | | |
| Rebound RT | % | 21.0 | 20.7 | 21.7 | 20.5 | 21.2 | 20.4 |
| Rebound 70° C. | % | 45.5 | 40.5 | 43.4 | 41.6 | 42.2 | 40.3 |
| E' max | MPa | 12.3 | 13.9 | 12.6 | 14.6 | 14.3 | 15.9 |
| E' min | MPa | 5.2 | 5.3 | 5.4 | 5.6 | 5.4 | 5.8 |
| E' mean | MPa | 8.5 | 9.2 | 8.7 | 9.6 | 9.4 | 10.2 |
| E* | MPa | 8.2 | 11.1 | 7.7 | 8.1 | 10.0 | 9.6 |
| Tan delta max | | 0.182 | 0.232 | 0.188 | 0.208 | 0.210 | 0.223 |
| Tan delta @ Tg | | 0.775 | 0.631 | 0.780 | 0.771 | 0.699 | 0.712 |
| Tan delta @ 0° C. | | 0.686 | 0.631 | 0.706 | 0.710 | 0.682 | 0.696 |
| Tan delta @ 60 C. | | 0.192 | 0.255 | 0.190 | 0.196 | 0.224 | 0.216 |

Reinforcement in rubber is evident by improvement in modulus and failure properties such as tensile strength, tear resistance, crack resistance, and abrasion resistance of the final vulcanizate. However, the best single criterion for reinforcement is Energy at Break or break energy. The energy at break is a measure of the area between the modulus-elongation curve and the elongation axis. Data from Table 3 show significant improvements' in the tensile strength, energy at break, crack growth (DeMattia pierced cycles to fail), while maintaining equivalent or better processing, physical, and dynamic properties, such as delta torque and cure time (T95), Shore A Hardness, and Tan delta at 60° C., respectively. For example, the energy at break of the cured rubber containing the silanes from Examples 1 and 3 were 19.80 and 27.73 J/cm, respectively. The energy at break of the rubber containing a mixture of 66 weight percent silane from Example 1 and 34 weight percent silane from Example 3 was 28.87 J/cm$^3$, representing an improvement in the range of 4 to 46 percent over either of the silanes from Example 1 and 3 used alone.

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto.

What is claimed is:

1. A particulate-filled rubber composition comprising:
   (i) at least one vulcanizable rubber;
   (ii) at least one silane-reactive particulate filler;
   (iii) at least one blocked mercaptosilane possessing two thioacyl groups, the blocked mercaptosilane having the formula:

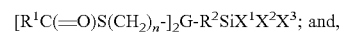
   $[R^1C(=O)S(CH_2)_n\text{-}]_2G\text{-}R^2SiX^1X^2X^3$; and, (iv) at least one blocked mercaptosilane possessing a single thioacyl group, the blocked mercaptosilane having the formula:

   $R^3C(=O)SR^4SiX^1X^2X^3$, wherein
   $R^1$ is methyl;
   $R^2$ is ethylene;
   $R^3$ is an alkyl group containing from 5 to 9 carbon atoms and bonded to the carbonyl group through a primary carbon atom;
   $R^4$ is propylene;
   G is a trivalent cyclohexane;
   $X^1$ is ethoxy;
   $X^2$ is ethoxy;
   $X^3$ is ethoxy; and,
   n is an integer 2, wherein blocked mercaptosilane (iii) is from 10 to 25 weight percent based on the total weight of blocked mercaptosilanes (iii) and (iv).

2. The particulate-filled rubber composition of claim 1 wherein the at least one sulfur-vulcanizable rubber (i) is selected from the group consisting of solution styrene-butadiene rubber (sSBR), solution styrene-butadiene rubber (sSBR) having bound styrene content in a range of 5 to 50 percent, solution styrene-butadiene rubber (sSBR) having bound styrene content in a range of 9 to 36 percent, emulsion polymerized styrene-butadiene rubber (eSBR), emulsion polymerized styrene-butadiene rubber (eSBR) having a styrene content of 20 to 28 percent bound styrene, emulsion polymerized styrene-butadiene rubber (eSBR) having a styrene content of 30 to 45 percent bound styrene, styrene-butadiene rubber (SBR), natural rubber (NR), polybutadiene (BR), polybutadiene (BR)containing 90 weight percent cis-1,4-content, ethylene-propylene co- and ter- polymers (EP, EPDM), acrylonitrile-butadiene rubber (NBR), cis-1,4-polyisoprene rubber, 3,4-polyisoprene rubber, isoprene/butadiene rubber, styrene/isoprene/butadiene terpolymer rubber, cis-1,4-polybutadiene, medium vinyl polybutadiene rubber containing 35 percent to 50 percent vinyl, high vinyl polybutadiene rubber containing 50 percent to 75 percent vinyl, styrene/isoprene copolymers, emulsion polymerization prepared styrene/butadiene/acrylonitrile terpolymer rubber and butadiene/acrylonitrile copolymer rubber.

3. The particulate-filled rubber composition of claim 1 wherein silane-reactive particulate filler (ii) is selected from the group consisting of pyrogenic silica, precipitated silica, titanium dioxide, aluminosilicate, alumina, clays, talc and mixtures thereof.

4. The particulate-filled rubber composition of claim 3 wherein the total amount of silane-reactive particulate filler (ii) is from 5 to 140 phr.

5. The particulate-filled rubber composition of claim 1 wherein blocked mercaptosilane (iv) is 3-triethoxysilylpropyl thiooctanoate.

6. The particulate-filled rubber composition of claim 1 wherein the total amount of the blocked mercaptosilanes (iii) and (iv) is from 0.2 to 12 parts by weight per hundred parts by weight of rubber.

7. The particulate-filled rubber composition of claim 1 wherein blocked mercaptosilane (iii) is 4-(2-triethoxysilylethyl)-1,2-bis-(3-thia-4-oxopentyl)cyclohexane and blocked mercaptosilane (iv) is 3-triethoxysilylpropyl thiooctanoate.

8. The particulate-filled rubber composition of claim 1 further comprising at least one additional component selected from the group consisting of inert particulate filler(s), curing aid(s), activator(s), retarder(s), accelerator(s), processing additive(s), resin(s), plasticizer(s), pigment(s), fatty acid(s), zinc oxide, wax(es), antioxidant(s), antiozonant(s) and peptizing agent(s).

9. The particulate-filled rubber composition of claim 1 wherein the amount of silane-reactive filler (ii) is from 5 to 140 parts per hundred parts by weight rubber, and the total amount of blocked mercaptosilane (iii) and blocked mercaptosilane (iv) is from 0.05 to 25 parts by weight per hundred parts by weight of rubber.

10. The particulate-filled rubber composition of claim 9 wherein said particulate-filled rubber is selected from the group consisting of:
(1) particulate-filled rubber composition comprising components (i), at least part of (ii), at least part of (iii), at least part of (iv) and the remainder of (ii) pre-reacted with the remainder of (iii) and the remainder of (iv);
(2) particulate-filled rubber composition comprising components (i), at least part of (ii), at least part of (iv) and the remainder of (ii) pre-reacted with all of (iii) and the remainder of (iv);
(3) particulate-filled rubber composition comprising components (i), at least part of (ii), at least part of (iii) and the remainder of (ii) pre-reacted with the remainder of (iii) and all of (iv);
(4) particulate-filled rubber composition comprising components (i), at least part of (iii), at least part of (iv) and all of (ii) pre-reacted with the remainder of (iii) and the remainder of (iv);
(5) particulate-filled rubber composition comprising components (i), at least part of (iv) and all of (ii) pre-reacted with all of (iii) and the remainder of (iv);
(6) particulate-filled rubber composition comprising (i), at least part of (iii) and all of (ii) pre-reacted with the remainder of (iii) and all of (iv); and,
(7) particulate-filled rubber composition comprising (i) and all of (ii) pre-reacted with all of (iii) and all of (iv).

11. The vulcanized rubber composition of claim 1.
12. The vulcanized rubber composition of claim 8.
13. The vulcanized rubber composition of claim 9.
14. The vulcanized rubber composition of claim 10.
15. An article made from the particulate filled rubber composition of claim 1.
16. The article of claim 15 which is a tire, tire component, hose, belt, roller, insulation, jacketing, industrial good, shoe sole, bushing or damping pad.
17. An article made from the particulate filled rubber composition of claim 8.
18. The article of claim 17 which is a tire, tire component, hose, belt, roller, insulation, jacketing, industrial good, shoe sole, bushing or damping pad.
19. An article made from the particulate filled rubber composition of claim 9.
20. The article of claim 19 which is a tire, tire component, hose, belt, roller, insulation, jacketing, industrial good, shoe sole, bushing or damping pad.
21. An article made from the particulate filled rubber composition of claim 10.
22. The article of claim 21 which is a tire, tire component, hose, belt, roller, insulation, jacketing, industrial good, shoe sole, bushing or damping pad.
23. A free-flowing filler composition comprising the particulate-filled rubber composition of claim 1.
24. A process for making the particulate-filled rubber composition of claim 1 comprising:
a) thermomechanically mixing, components (i), (ii), (iii) and (iv) of claim 1 at a first elevated temperature in at least one preparatory mixing step
b) blending the mixture result from (a) with at least one acyl-reactive deblocking agent and, optionally, at least one vulcanization agent, at a second elevated temperature which is below the first elevated temperature; and, optionally,
c) curing said mixture at a third elevated temperature and for a period of time sufficient to effect curing of the mixture resulting from (b).

25. The process of claim 24, wherein blocked mercaptosilane (iii) is 4-(2-triethoxysilylethyl)-1,2-bis-(3-thia-4-oxopentyl)clohexane.

26. The process of claim 24 wherein blocked mercaptosilane (iv) is 3-triethoxysilylpropyl thiooctanoate.

27. The process of claim 24 wherein in step (a), (i) 100 parts by weight of vulcanizable rubber selected from the group consisting of conjugated diene homopolymers, conjugated diene copolymer, copolymer of at least one conjugated dime of at least one aromatic vinyl compound and mixtures thereof are mixed with (ii) from 5 to 140 parts per hundred parts by weight rubber of at least one silane-reactive particulate filler or a mixture of from 15 to 99 weight percent at least one silane-reactive particulate filler and, correspondingly, from 1 to 85 weight percent of at least one inert particulate filler and (iii) from 0.05 to 25 parts per hundred part by weight rubber in the total of blocked mercaptosilane (iii) and blocked mercaptosilane (iv).

28. The process of claim 24 wherein at least part up to the full amount of silane-reactive filler (ii), at least part up to the full amount of blocked mercaptosilane (iii) and at least part up to the full amount of blocked mercaptosilane (iv) are provided as the reaction product of silane-reactive particulate filler (ii) and mixture of blocked mercaptosilane (iii) and blocked mercaptosilane (iv).

* * * * *